US007811760B2

(12) United States Patent
Akahoshi et al.

(10) Patent No.: US 7,811,760 B2
(45) Date of Patent: Oct. 12, 2010

(54) VECTOR AND METHOD FOR DETECTING THE CHANGE IN TRANSCRIPTION AMOUNT

(75) Inventors: Eiichi Akahoshi, Kawasaki (JP); Seiko Yoshimura, Tokyo (JP); Mitsuko Ishihara, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 597 days.

(21) Appl. No.: 11/617,282

(22) Filed: Dec. 28, 2006

(65) Prior Publication Data

US 2008/0003596 A1 Jan. 3, 2008

(30) Foreign Application Priority Data

Jan. 4, 2006 (JP) ............................. 2006-000135

(51) Int. Cl.
| | |
|---|---|
| *C12Q 1/68* | (2006.01) |
| *C12Q 1/66* | (2006.01) |
| *C12Q 1/54* | (2006.01) |
| *C12Q 1/48* | (2006.01) |
| *C12Q 1/34* | (2006.01) |
| *C12Q 1/02* | (2006.01) |
| *C12N 15/00* | (2006.01) |
| *C12N 15/113* | (2006.01) |
| *C12N 5/07* | (2006.01) |
| *C12N 5/071* | (2006.01) |
| *C12N 5/079* | (2006.01) |

(52) U.S. Cl. .................. 435/6; 435/8; 435/14; 435/15; 435/18; 435/29; 435/320.1; 435/325; 435/354; 536/24.1

(58) Field of Classification Search ....................... None
See application file for complete search history.

(56) References Cited

U.S. PATENT DOCUMENTS

| | | | |
|---|---|---|---|
| 5,854,010 | A | 12/1998 | Denison et al. |
| 6,504,080 | B1 | 1/2003 | Van Der Putten |
| 7,413,898 | B2 * | 8/2008 | Yoshimura et al. .......... 435/325 |
| 2006/0275275 | A1 | 12/2006 | Yoshimura et al. |

FOREIGN PATENT DOCUMENTS

| | | |
|---|---|---|
| JP | 2000-253889 | 9/2000 |
| JP | 2000-300258 | 10/2000 |
| JP | 2000-300259 | 10/2000 |
| JP | 2002-253231 | 9/2002 |

OTHER PUBLICATIONS

Maharjan et al. Transcriptional regulation of tyrosine hydroxylase by estrogen: opposite effects with estrogen receptors alpha and beta and interactions with cyclic AMP. Journal of Neurochemistry, vol. 93, pp. 1502-1514, Jun. 2005.*
Jeong et al. Regulation of the transcriptional activity of the tyrosine hydroxylase gene by androgen receptor. Neuroscience Letters, vol. 396, pp. 57-61, Mar. 2006.*
Hagerty et al. Identification of a glucocorticoid-responsive element in the promoter region of the mouse tyrosine hydroxylase gene. Journal of Neurochemistry, vol. 76, pp. 825-834, 2001.*
GenBank Accession No. X53503, GI: 55055, publicly available Apr. 2005.*
GenBank Accession No. AC012382.14, GI:12740210, publicly available Feb. 2001.*
Gandelman et al. Species and regional differences in expression of cell-type specific elements oat the human and rat tyrosine hydroxylase gene loci. Journal of Neurochemistry, vol. 55, pp. 2149-2152, 1990.*
Eguchi et al. Molecular cloning of the human AH receptor gene promoter. Biochemical and Biophysical Research Communications, vol. 203, No. 1, pp. 615-622, Aug. 1994.*
Cazorla et al. A response element for the homeodomain transcription factor Ptx3 in the tyrosine hydroxylase gene promoter. Journal of Neurochemistry, vol. 74, pp. 1829-1837, 2000.*
Yang et al. Regulatory interaction between arylhydrocarbon receptor and SIM1, two basic helix-loop-hilix PAS proteins involved in the control of food intake. The Journal of Biological Chemistry, vol. 279, No. 10, pp. 9306-9312, Mar. 2004.*
Vinals et al. BMP-2 decreases Mash1 stability by increasing Id1 expression. The EMBO Journal, vol. 23, pp. 3527-3537, Aug. 2004.*
Alexander et al. Ah receptor regulation of CYP1B1 expression in primary mouse embryo-derived cells. Cancer Research, vol. 57, pp. 4498-4506, Oct. 1997.*
Jeong et al. Regulation of the transcrptional activity of the tyrosine hydroxylase gene by androgen receptor. Neuroscience Letters, vol. 396, pp. 57-61, published online Dec. 13, 2005.*
Perdew, GH. Association of the Ah receptor with the 90-kDa heat shock protein. The Journal of Biological Chemistry, vol. 263, No. 27, pp. 13802-13806, Sep. 1988.*
Alexaki et al. Estrogen exerts neuroprotective effects via membrane estrogen receptors and rapid Akt/NOS activation. The FASEB Journal, vol. 18, No. 13, pp. 1594-1596, article 10.1096/fj.04-1495fje. Published online Aug. 2, 2004.*
Thanky et al. Sex differences in the regulation of tyrosine hydroxylase gene transcription by estrogen in the locus coeruleus of TH9-LacZ transgenic mice. Molecular Brain Research, vol. 104, pp. 220-226, 2002.*
Seegal et al. Effects of in utero and lactational exposure of the laboratory rat to 2,4,2',4'- and 3,4,3',4'-tetrachlorobiphenyl on dopamine function. Toxicology and Applied Pharmacology, vol. 146, pp. 95-103, 1997.*
U.S. Appl. No. 12/559,303, filed Sep. 14, 2009, Akahoshi, et al.
Shreekrishna Maharjan, et al., "Transcriptional regulation of tyrosine hydroxylase by estrogen: opposite effects with estrogen receptors α and β and interactions with cyclic AMP", International Society for Neurochemistry, Journal of Neurochemistry, 93, 2005, pp. 1502-1514.
Eiichi Akahoshi, et al., "Over-expression of AhR (aryl hydrocarbon receptor) induces neural differentiation of Neuro2a cells: neurotoxicology study", Environmental Health: A Global Access Science Source, BioMed Central, Sep. 7, 2006, 11 Pages.

* cited by examiner

*Primary Examiner*—Jennifer Dunston
(74) *Attorney, Agent, or Firm*—Oblon, Spivak, McClelland, Maier & Neustadt, L.L.P.

(57) ABSTRACT

A vector includes an enhancer region derived from a transcriptional regulatory region of tyrosine hydroxylase gene wherein the enhancer region enhances transcription amount of a downstream gene in response to a test substance, a promoter which is functionally linked to downstream of the enhancer region, and a reporter gene which is functionally linked to downstream of the promoter.

60 Claims, 9 Drawing Sheets

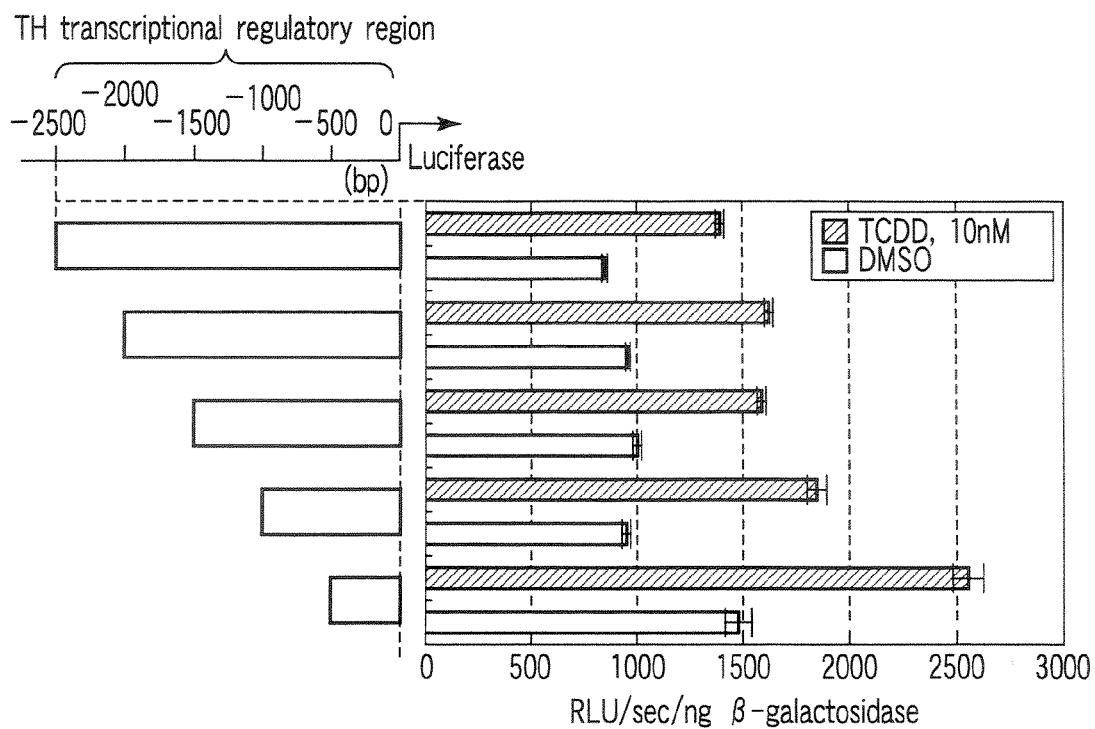
F I G. 3
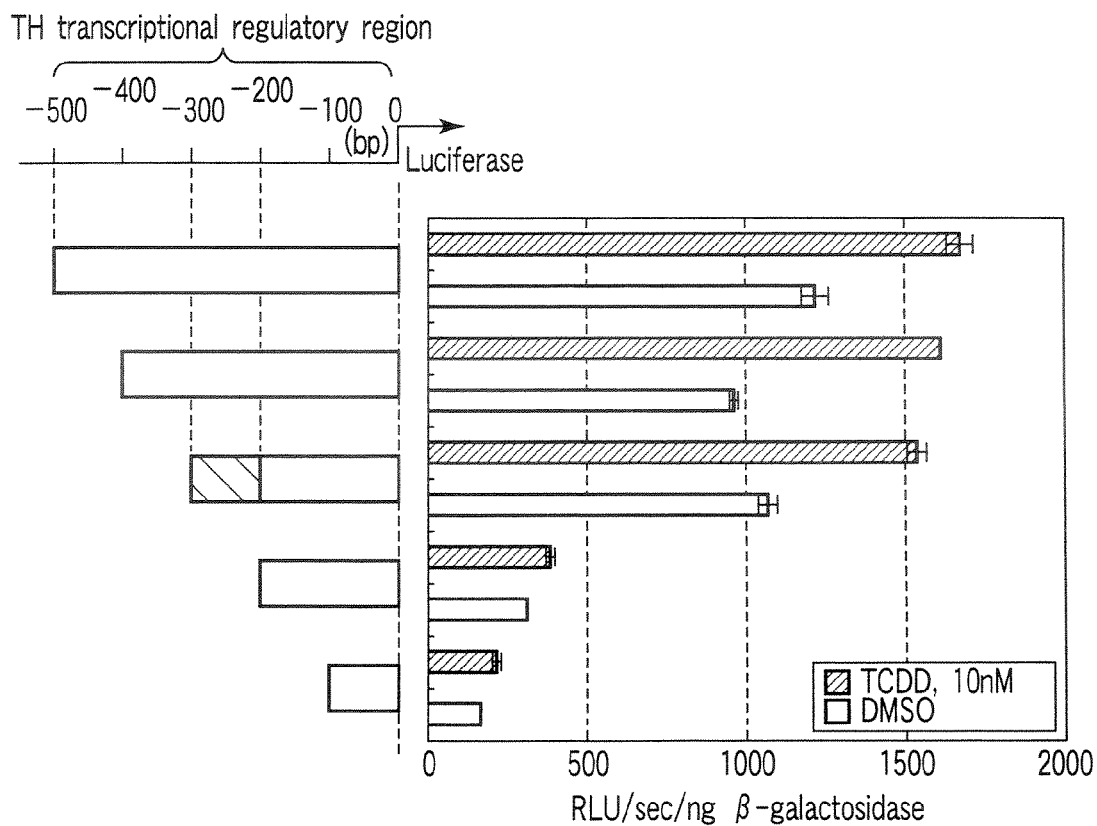
F I G. 4

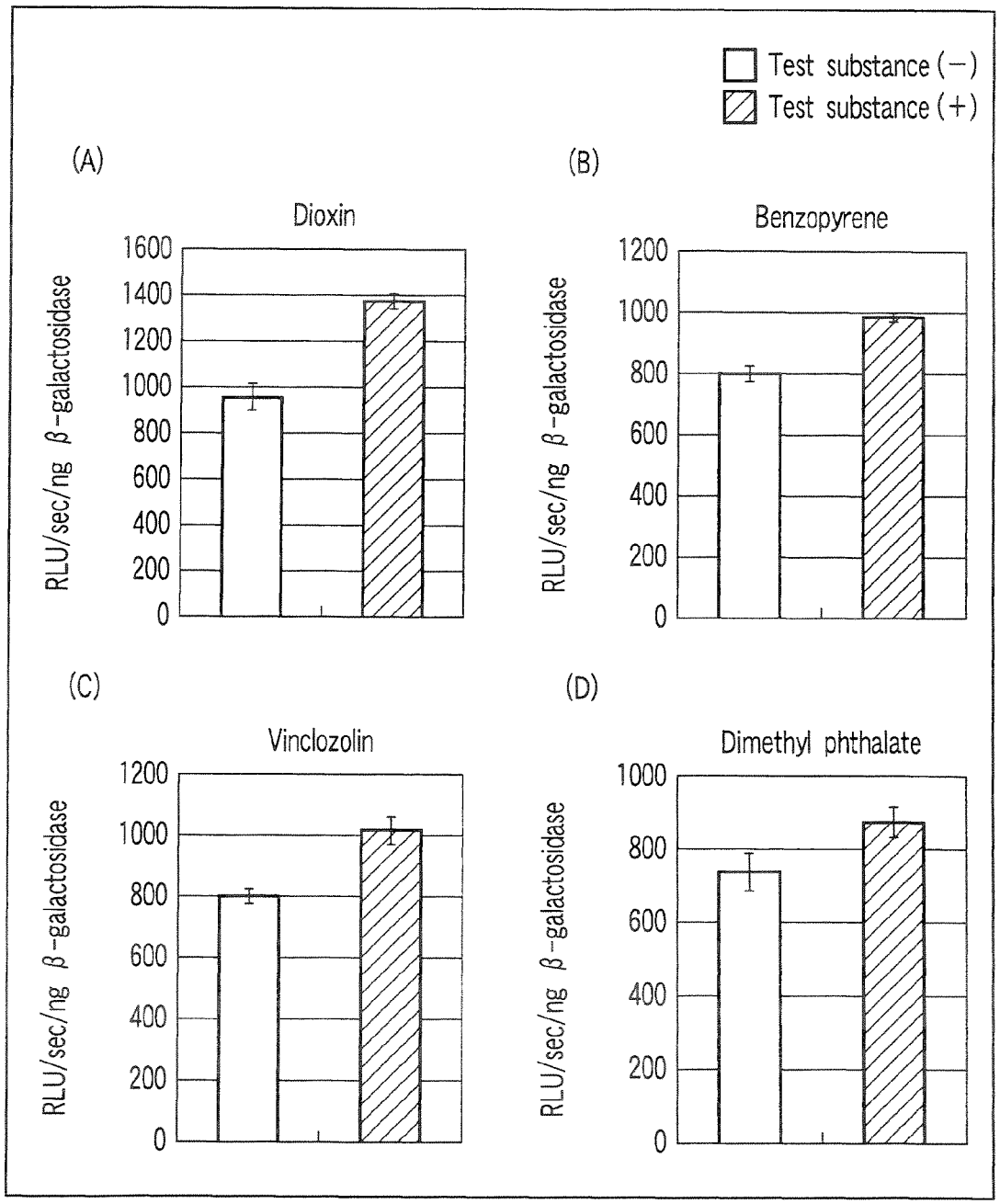
F I G. 5

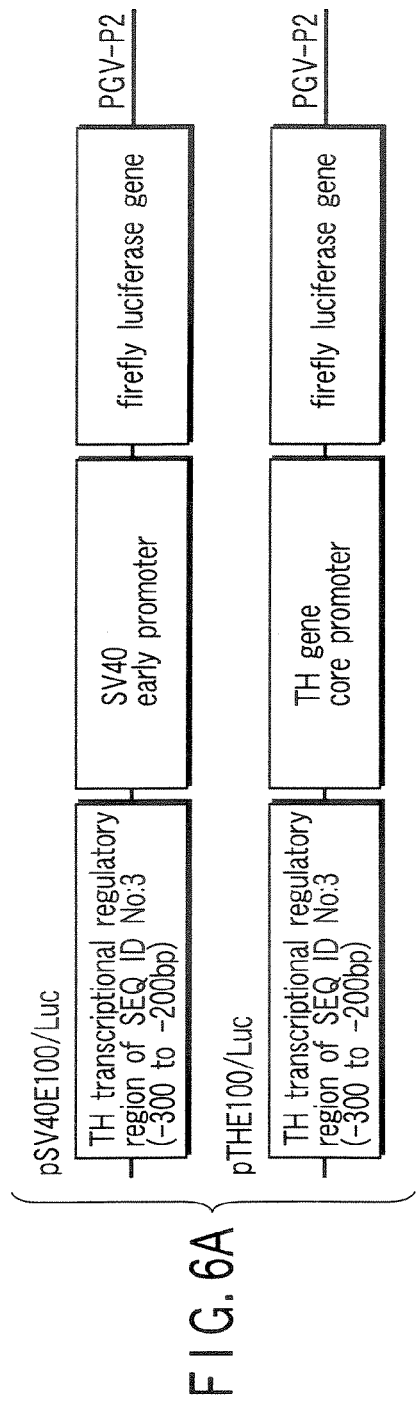
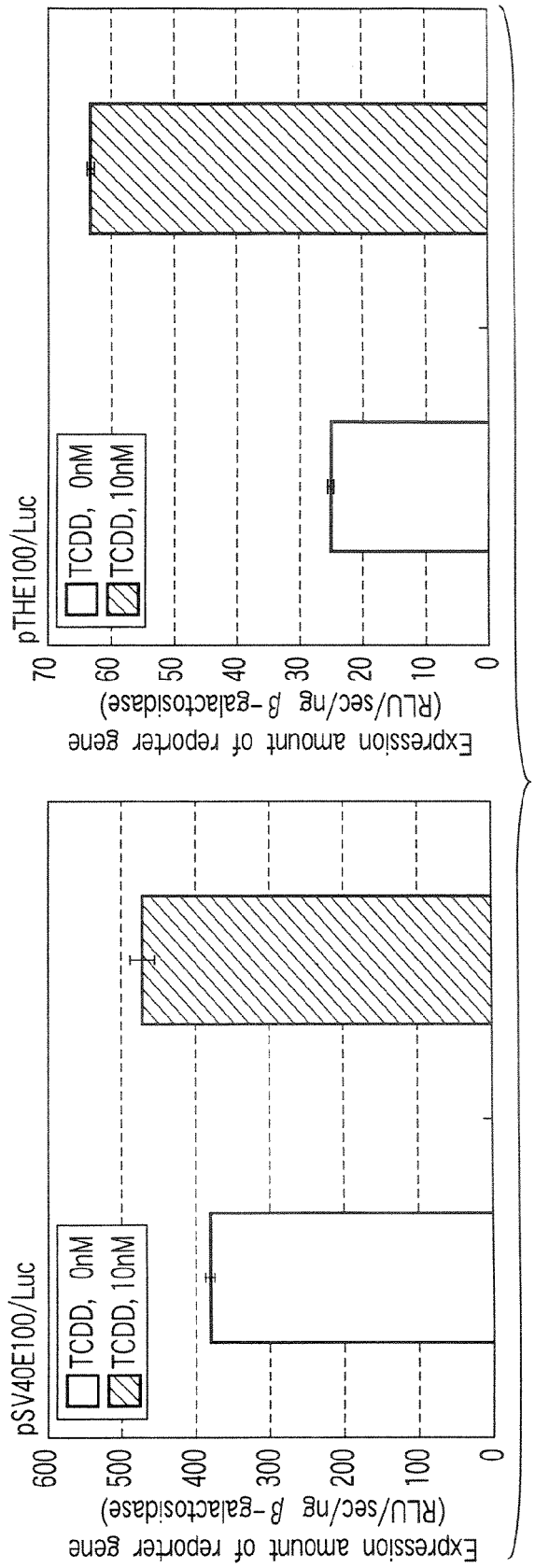
F I G. 6A
F I G. 6B

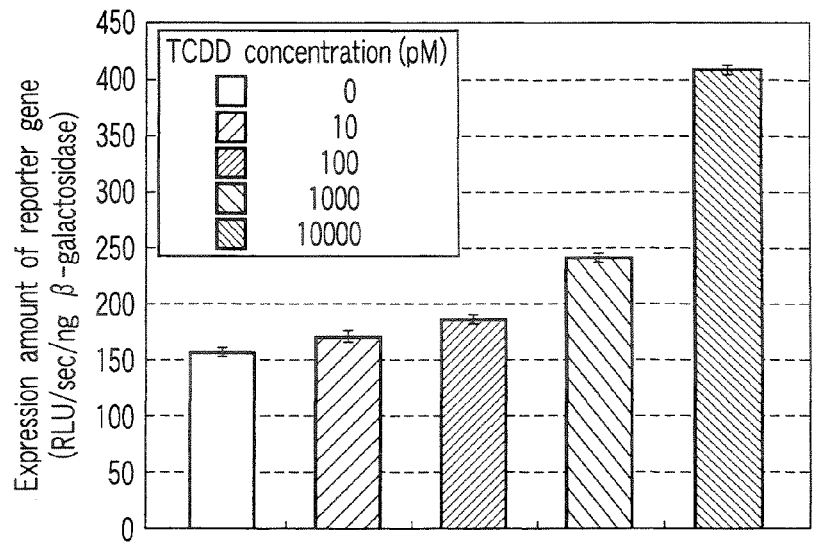
F I G. 8A
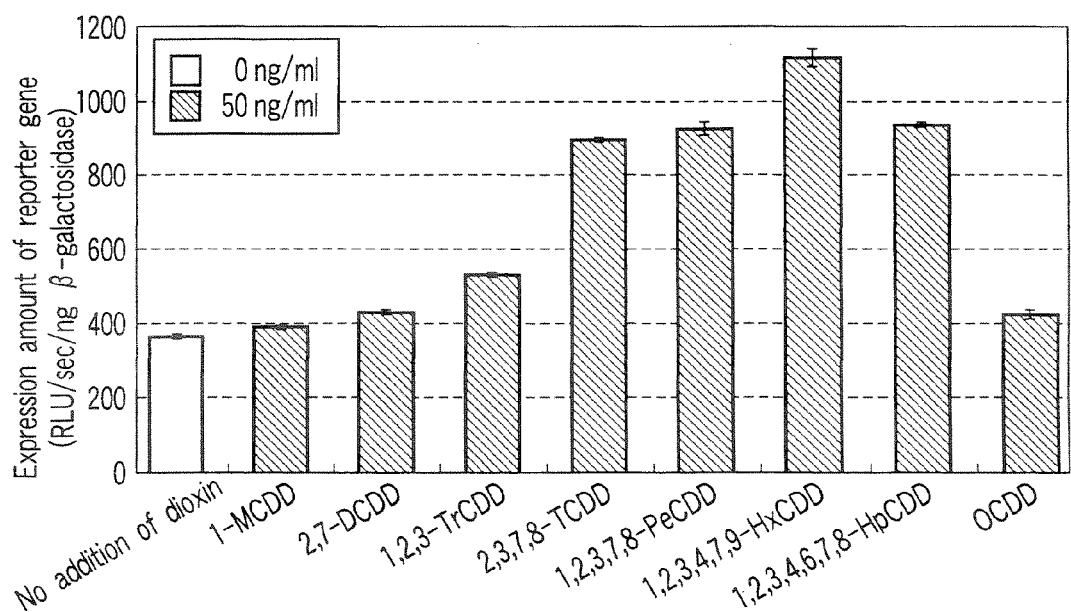
F I G. 8B

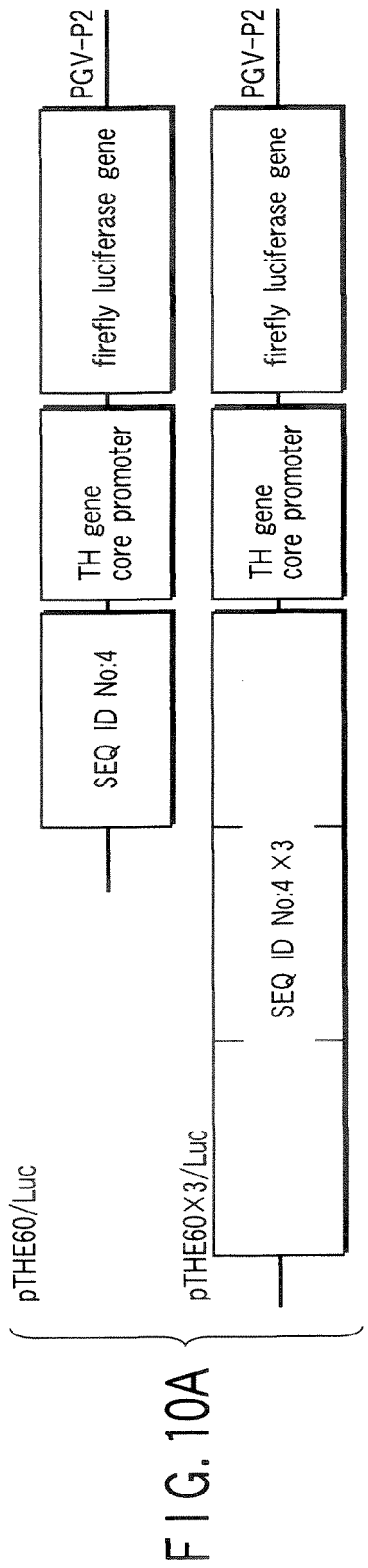
F I G. 10A
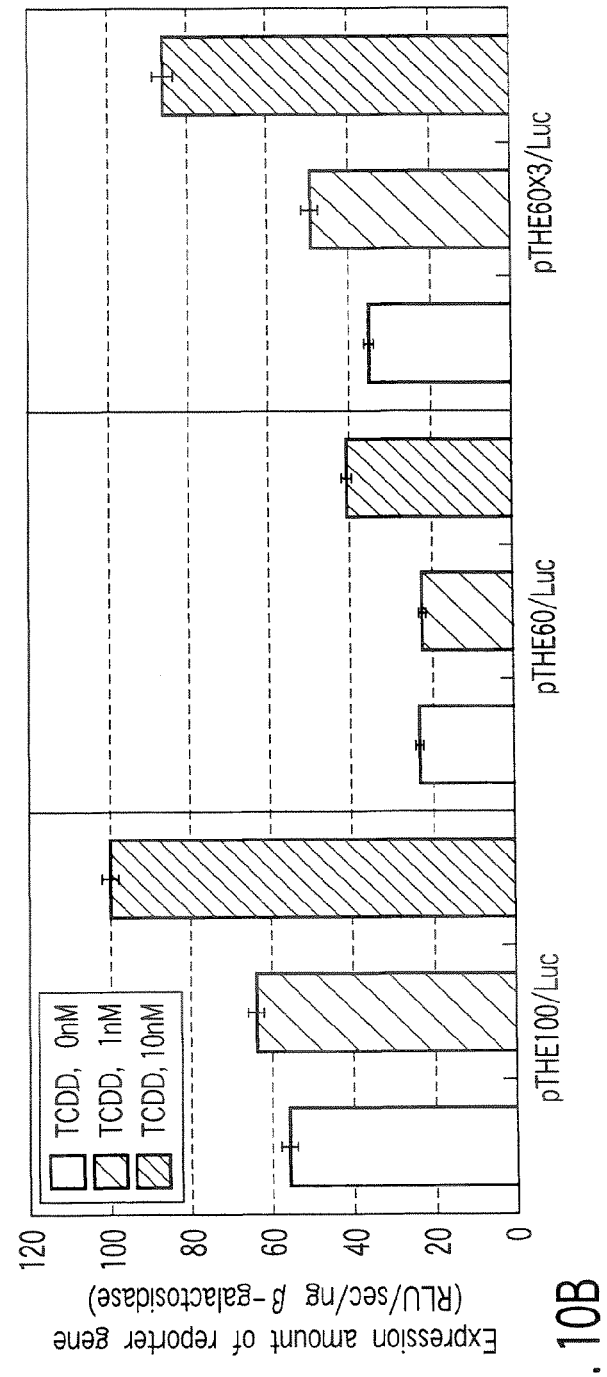
F I G. 10B

VECTOR AND METHOD FOR DETECTING THE CHANGE IN TRANSCRIPTION AMOUNT

CROSS-REFERENCE TO RELATED APPLICATIONS

This application is based upon and claims the benefit of priority from prior Japanese Patent Application No. 2006-000135, filed Jan. 4, 2006, the entire contents of which are incorporated herein by reference.

BACKGROUND OF THE INVENTION

1. Field of the Invention

The present invention relates to a vector and a method for detecting the action of a test substance on the gene transcription by activation of the ligand-dependent transcription factor corresponding to the test substance.

2. Description of the Related Art

Along with the progress in human domestic and industrial activities, there exists a serious social problem of adverse influences on the body by the chemical substances released into the environment. Currently, there are estimated to be at least 100,000 types of chemicals that are commercially produced, and in addition, there are still various types of chemicals that are unintendedly released into the environment in the human productive activities. The influence of most of these chemicals on the human body is unknown, and there is a concern about the diseases caused by these chemicals.

Among the chemicals present in the environment, the influence of the chemicals acting on nuclear receptors, i.e., ligand-dependent transcription factors, on the human body is more serious. The ligand-dependent transcription factors are proteins that have a function to change the transcription efficiency of a target gene on chromosome, wherein the proteins are activated by binding to a substrate, and bind to the recognition sequence present in the transcriptional regulatory region of the target gene. These ligand-dependent transcription factors play important roles in maintenance of homeostasis, reproduction, development, cell differentiation, and drug metabolism of organisms. Improper transcriptional regulation of a target gene by a transcription factor is known to cause abnormality in the expressed amount of the gene and hence various diseases. A method for measuring the activity of a chemical substance on the transcriptional regulatory potential of a ligand-dependent transcription factor is under development, for the purpose of restricting intake of chemical substances that induce diseases as a result of improper transcriptional regulation, or for the treatment and prevention of the diseases caused by such chemical substances, by detecting these chemical substances from among the chemicals present in the environment.

For example, for measurement of the activity of a test substance on the transcriptional regulatory potential, known is a method for measuring the activity of a test substance on the transcriptional regulation of a ligand-dependent transcription factor, by introducing a vector containing a reporter gene linked to downstream of the recognition sequence of a ligand-dependent transcription factor, and measuring the expressed amount of the reporter gene after the cell is incubated in the presence of the test substance. For measurement of the activity of a test substance similar to polycyclic aromatic hydrocarbons (PAHs) in structure, there has been proposed a method of measuring the activity of a test substance on the aryl hydrocarbon receptor (AhR)-mediated transcriptional regulation, by using a cell containing a vector having a reporter gene linked to downstream of a recognition sequence (i.e., xenobiotic responsive element (XRE)) for an aryl hydrocarbon receptor (AhR) which uses the PAHs as substrates. (JP-A 2000-253889 (KOKAI) and U.S. Pat. No. 5,854,010). Alternatively, for measurement of the influence of a test substance on a reproductive function, there has been proposed a method of measuring the activity of a test substance on female-hormone (estrogen) receptor (ER) or male-hormone (androgen) receptor (AR)-mediated transcription regulation, by using a cell containing a vector having a reporter gene linked to downstream of a recognition sequence for ER, i.e., estrogen responsive sequence (ERE), or a recognition sequence for AR, i.e., androgen responsive sequence (ARE) (JP-A 2002-253231 (KOKAI)). ER and AR are ligand-dependent transcription factors for controlling the reproductive function.

However, these methods only allow detection of the influence of the test substance on only one kind of ligand-dependent transcription factor-mediated transcriptional activation, by using one type of vector. In other words, these methods allow detection of the influence of the test substance on ligand-dependent transcription factor-mediated transcriptional activation, only by detecting separately the binding of each of activated transcription factors AhR, ER and AR to the corresponding recognition sequences XRE, ERE and ARE.

BRIEF SUMMARY OF THE INVENTION

According to an aspect of the present invention, there is provided a vector comprising: an enhancer region derived from a nucleotide sequence shown by SEQ ID No: 1 (transcriptional regulatory region of tyrosine hydroxylase (TH) gene) wherein the enhancer region enhances the transcription amount of a downstream gene in response to a test substance; a promoter functionally linked to downstream of the enhancer region; and a reporter gene functionally linked to downstream of the promoter.

According to another aspect of the present invention, there is provided a transfected mammalian cell comprising the vector introduced therein.

According to yet another aspect of the present invention, there is provided a kit for detection of a dioxin-, estrogen-, or androgen-like activity of a test substance, the kit comprising the vector or the cell.

According to yet another aspect of the present invention, there is provided a method of detecting a dioxin-, estrogen-, or androgen-like activity of a test substance, the method comprising: (1) a step of culturing a cell comprising the vector introduced therein, in the presence of a test substance and in the absence of the test substance, respectively; (2) a step of measuring the expressed amount of the reporter gene (contained in the vector) in the cell cultured in the step (1); and (3) a step of evaluating that the test substance has a dioxin-, estrogen- or androgen-like activity, when the measured value of the expressed amount of the reporter gene in the cell cultured in the presence of a test substance is greater than that of the reporter gene in the cell cultured in the absence of the test substance.

BRIEF DESCRIPTION OF THE SEVERAL VIEWS OF THE DRAWING

FIG. 3 is a graph showing the amounts of a reporter gene-product expressed after TCDD exposure in the case of using the vectors according to an embodiment of the present invention having TH transcriptional regulatory regions different in length;

FIG. 4 is a graph showing the amounts of a reporter gene-product expressed after TCDD exposure in the case of using the vectors according to an embodiment of the present invention having TH transcriptional regulatory regions different in length;

FIG. 5 shows graphs (A) to (D) showing the amounts of the reporter gene-product expressed by the vector according to an embodiment of the present invention in the presence of a test substance;

FIG. 6A is a schematic diagram illustrating vectors pSV40E100/LUC and pTHE100/LUC according to an embodiment of the present invention containing a TH transcriptional regulatory region shown by SEQ ID No: 3, and FIG. 6B shows graphs showing the amounts of a reporter gene-product expressed by the vectors in the presence of a test substance TCDD;

FIG. 8A is a graph showing the relationship between the response of the vector according to an embodiment of the present invention and the TCDD concentration, and FIG. 8B is a graph showing the response of the vector according to an embodiment of the present invention to various types of dioxins;

FIG. 10A is a schematic diagram showing a vector pTHE60/Luc according to an embodiment of the present invention containing the TH transcriptional regulatory region of SEQ ID No: 4 and a vector pTHE60×3/LUC according to an embodiment of the present invention containing the tandem repeats of SEQ ID No: 4, and FIG. 10B is a graph showing the amounts of reporter gene-product expressed by the vectors in the presence of a test substance TCDD.

DETAILED DESCRIPTION OF THE INVENTION

After intensive studies, the inventors have found that it is possible to detect the influence of a test substance on the gene transcription mediated by activation of aryl hydrocarbon receptor, estrogen receptor, and androgen receptor, by performing a reporter gene assay using a cell containing a vector having a part of a transcriptional regulatory region of a tyrosine hydroxylase (TH) gene, and a promoter and a reporter gene functionally linked to downstream of the transcriptional regulatory region. As a result, the inventors completed the present invention. The present invention provides a method allowing detection of the gene transcription mediated by multiple types of ligand-dependent transcription factors, by using one type of vector.

1. Vector

Hereinafter, a vector according to the present invention will be described in detail.

The vector according to the present invention contains an enhancer region derived from a transcriptional regulatory region of a tyrosine hydroxylase (TH) gene wherein the enhancer region enhances the transcription amount of its downstream gene in response to a test substance, and a promoter and a reporter gene functionally linked to downstream of the enhancer region.

(1) Enhancer Region

The transcriptional regulatory region of tyrosine hydroxylase (TH) gene is, for example, the region (2.5 kb) shown by SEQ ID No: 1. In the present invention, the "transcriptional regulatory region of tyrosine hydroxylase (TH) gene" may be a 5'-upstream region (2,500 bp) of the tyrosine hydroxylase gene of any organism, for example, a 5'-upstream region (2,500 bp) of the tyrosine hydroxylase gene of human, mouse, or rat.

Figure 11:
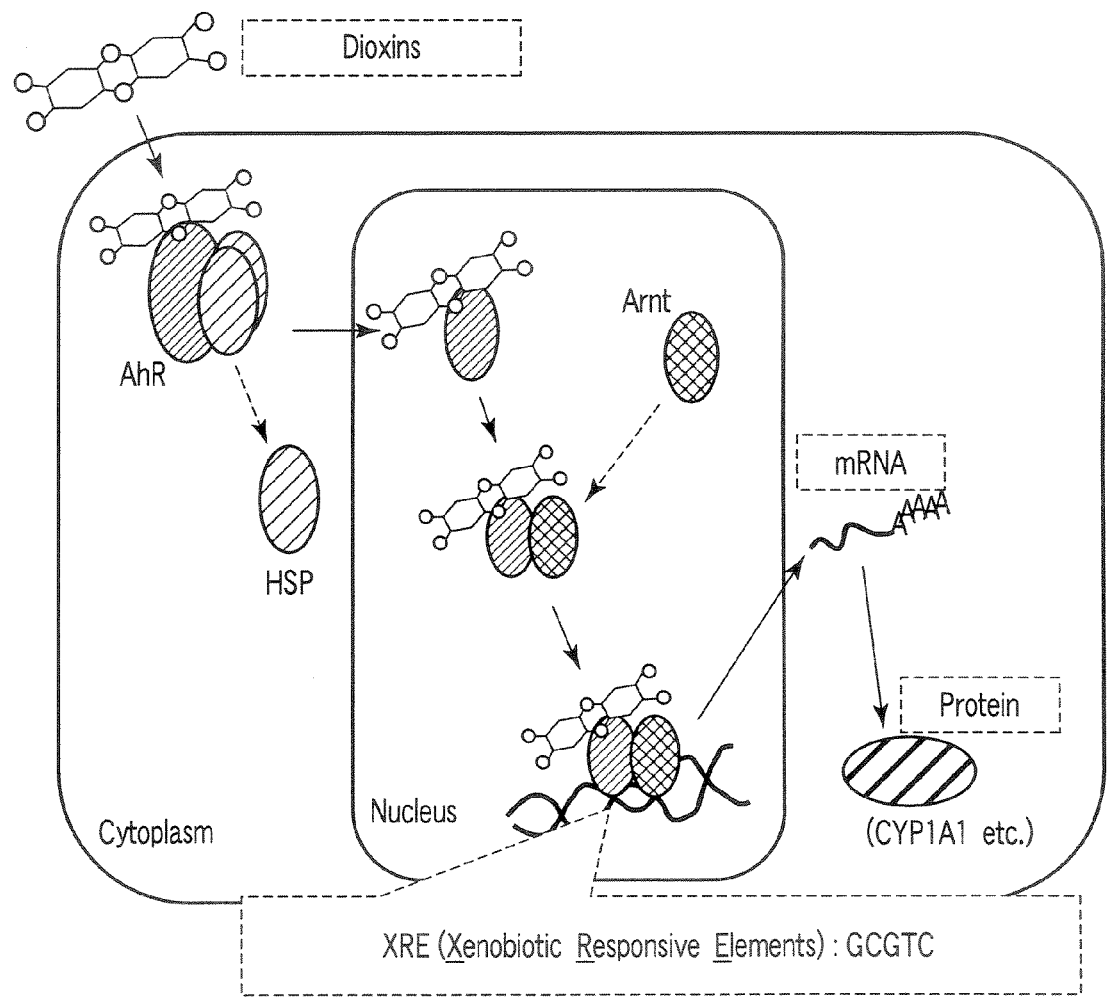
FIG. 11 is a schematic diagram showing the mechanism of dioxins activating transcription of a gene via an aryl hydrocarbon receptor (AhR).

In the present invention, the test substance may be any substance that is suspected of having a dioxin-, estrogen-, or androgen-like activity. In the present invention, the inventors have found that each of the substance having dioxin-like activity, the substance having estrogen-like activity and the substance having androgen-like activity can act on the enhancer region to enhance the transcription amount of the downstream gene. It is estimated that a substance having dioxin-like activity forms a complex with an aryl hydrocarbon receptor and the complex binds to the enhancer region, thereby enhancing the transcription amount of the downstream gene. FIG. 11 shows one of the mechanism of the gene transcriptional activation mediated by an aryl hydrocarbon receptor (AhR). Dioxins such as TCDD are known to activate expression of the downstream genes (for example, drug-metabolizing enzyme CYP1A1) by forming a complex with an aryl hydrocarbon receptor (AhR) in a cell and binding to a particular nucleotide sequence (i.e., a xenobiotic responsive element XRE: 5'-GCGTG-3'). In FIG. 11, HSP represents a heat shock protein, and Arnt represents an aryl hydrocarbon receptor nuclear translocator. Similarly, a substance having estrogen-like activity is known to activate expression of the downstream genes by forming a complex with an estrogen receptor in a cell and binding to a particular nucleotide sequence (i.e., an estrogen responsive element ERE: 5'-GGTCAnnnTGACC-3' (SEQ ID NO: 31), where "n" represents any nucleotide). A substance having androgen-like activity is known to activate expression of the downstream genes by forming a complex with an androgen receptor in a cell and binding to a particular nucleotide sequence (i.e., an androgen responsive element ARE: 5'-GG[A or T]ACAnnnTGTTCT-3' (SEQ ID NO: 32), where "n" represents any nucleotide).

The "enhancer region enhancing transcription amount of a downstream gene in response to a test substance" may be the entire region of the sequence shown by SEQ ID No: 1, or alternatively, may be part of the sequence shown by SEQ ID No: 1 that enhances the gene transcription in response to the test substance. In the present specification, the phrase "enhance (enhancing) transcription amount of a gene in response to a test substance" means that, when a cell containing the vector according to the present invention is cultured in the presence of a test substance, the expression amount of a reporter gene functionally linked to downstream of the enhancer region is increased.

The "enhancer region enhancing transcription amount of a gene in response to a test substance" is, for example, the region of the sequence (315 bp) shown by SEQ ID No: 2, the region of the sequence (143 bp) shown by SEQ ID No: 3, and the region of the sequence (67 bp) shown by SEQ ID No: 4. The entire length of each of the nucleotide sequences of SEQ. ID. No: 1 to 3 may be used as enhancer regions, but a partial region thereof may be used if it contains a region equivalent to the sequence (67 bp) of SEQ ID No: 4.

The region of the sequence shown by SEQ ID No: 2 includes both a region enhancing a promoter activity and a region having the promoter activity. On the other hand, the region of the sequence shown by SEQ ID No: 3 includes a region enhancing a promoter activity but not a region having the promoter activity. The region of the sequence shown by SEQ ID No: 4 includes a region enhancing the promoter activity, but does not contain a region having a promoter activity. Thus, the "enhancer region enhancing transcription amount of a gene in response to the test substance" may contain a region having a promoter activity as in the sequence shown by SEQ ID No: 2 or may not contain the region having the promoter activity as in the sequence shown by SEQ ID No: 3 and 4. It would be obvious to a person skilled in the art that the transcriptional regulatory region in the sequence shown by SEQ ID No: 1 is not a region strictly defined but a region defined with some flexibility. For example, it is possible to identify the "enhancer region enhancing transcription amount of a gene in response to a test substance" easily by preparing and using a transcriptional regulatory region having a sequence shorter than the full length of the sequence shown by SEQ ID No: 1. Specifically, as shown in Examples below, a vector is prepared by amplifying a shorter region than the TH gene transcriptional regulatory region having a length of approximately 2.5 kbp by means of PCR using the 2.5 kbp region as a template, and functionally incorporating the shorter region into the vector according to the present invention. The vector containing the shorter transcriptional regulatory region is then introduced into a cell. The vector-carrying cell is then cultured with a test substance, and the expression amount of the reporter gene is analyzed. If the expression amount of the reporter gene is found to be greater than that expressed in a cell cultured in the absence of the test substance, the shorter transcriptional regulatory region is identified as an "enhancer region enhancing transcription amount of a gene in response to a test substance".

The "enhancer regions enhancing transcription amount of a gene in response to a test substance" includes not only the region of the sequence shown by SEQ ID No: 1, or partial region of the sequence shown by SEQ ID No: 1, wherein these region enhance the gene transcription amount in response to a test substance, but also a region or a partial region of a sequence substantially same as the sequence above, wherein these regions enhance the gene transcription amount in response to a test substance. The phrase "sequence substantially same" means the sequence of SEQ ID No: 1 containing one or several mutations such as deletion, substitution or addition. Such mutant sequence may be obtained, for example, by point mutation method or PCR-based method using the sequence of SEQ ID No: 1. It is possible to confirm whether or not the obtained mutant sequence is the "region enhancing the gene transcription amount in response to a test substance" by performing a test as described above.

Further, the sequence shown by SEQ ID No: 1 is a mouse-derived TH gene transcriptional regulatory region, but a TH gene transcriptional regulatory region (corresponding to SEQ ID No: 1) derived from other species may be used instead.

The enhancer region may be contained in the vector according to the present invention as tandem repeats (see Examples 7 and 9 below). Specifically, the enhancer region shown by SEQ ID No: 3 or the enhancer region shown by SEQ ID No: 4 may be contained in the vector according to the present invention as tandem repeats. The repeat may consist of, for example, 2 to 10 enhancer regions. The repeat may contain enhancer regions in the normal direction (5'→3' direction) or enhancer regions in the reverse direction (3'→5' direction). For example, the repeat sequence may contain enhancer regions only in the normal direction (5'→3' direction), only in the reverse direction (3'→5' direction), or in a combination of the normal direction (5'→3' direction) and the reverse direction (3'→5' direction)

(2) Promoter

The vector according to the present invention includes the "enhancer region enhancing transcription amount of a gene in response to a test substance" and also a promoter and a reporter gene functionally linked to downstream of the enhancer region. The term "functionally linked" means that a linked region is linked such that the region exerts its specific function. For example, when a promoter is "functionally linked", the promoter is linked such that it exerts a promoter activity in the vector according to the present invention. When a reporter gene is "functionally linked", the reporter gene is linked such that it is expressed in the vector according to the present invention. Specifically, when a reporter gene is "functionally linked", the reporter gene is linked such that it is expressed in the vector according to the present invention by action of the enhancer region and the promoter.

The promoter in the present invention may be a promoter derived from the sequence shown by SEQ ID No: 1. For example, when the sequence of SEQ ID No: 1 or 2 is used as the enhancer region in the vector according to the present invention, these sequences already include a region having the promoter activity, and therefore may not include an additional promoter region.

On the other hand, when the sequence of SEQ ID No: 3 or 4 is used as the enhancer region, a region having the promoter activity should be incorporated into the vector according to the present invention. Any promoter may be used as the promoter if it functions in a host cell. Preferably, the promoter includes a promoter having an activity in a mammalian cell, for example, the core promoter of the tyrosine hydroxylase gene of SEQ ID No: 5. Other examples include simian virus 40 (SV40) early promoter (SEQ ID No: 6), simian virus 40 (SV40) late promoter (SEQ ID No: 7), human herpesvirus 1 thymidine kinase (TK) promoter (SEQ ID No: 8), Rous sarcoma virus (RSV) promoter, and a cytomegalovirus (CMV) promoter (SEQ ID No: 9) (see Example 6 below). It would be easy for a person skilled in the art to select a promoter suitable for a host organism.

(3) Reporter Gene

Any reporter gene known in the art may be used as the reporter gene in the present invention. The reporter gene is preferably a gene allowing simple measurement of the activity of its gene product at a low background noise. Example of the genes include luciferase gene allowing detection of the gene product by luminescence, green fluorescent protein gene allowing detection by fluorescence, β-galactosidase gene allowing detection by color development, and chloramphenicol-acetyltransferase gene allowing detection by the radiation activity.

(4) Other Elements

The vector according to the present invention may contain various other elements in addition to the above enhancer region, promoter and reporter gene. For example, an origin of replication (operating in a suitable microorganism) or a drug-resistance gene may be incorporated into the vector. Alternatively, a drug-resistance gene may be incorporated into the vector for the purpose of stably integrating the vector into chromosome in a cell. Examples of the drug-resistance genes include a zeocin-resistance gene and a hygromycin-resistance gene. The vector may also have a suitable restriction site such as a multicloning site.

The vector according to the present invention may be in any form: circular plasmid DNA, virus vector DNA, linear DNA fragment, or the like.

(5) Method of Preparing Vector

The vector can be prepared by any one of the methods known by a person skilled in the art, but may be prepared, for example, in the following manner.

(a) Preparation of Transcriptional Regulatory Region of Tyrosine Hydroxylase (TH) Gene A transcriptional regulatory region of a TH gene, whose nucleotide sequence is already known, can be isolated, for example, by using the polymerase chain reaction (PCR). For example, a genome DNA extracted from arbitrary cell may be used as a template for PCR. For example, the nucleotide sequence shown by SEQ ID No: 1 can be amplified by using a pair of primers shown in Examples below.

(b) Preparation of Vector

Then, the transcriptional regulatory region of the TH gene is incorporated into a vector. The vector is prepared by linking the transcriptional regulatory region of the TH gene prepared in (a) to a reporter gene in a manner allowing the reporter gene to function. It is preferable to confirm that there is no mutation in the nucleotide sequence of the transcriptional regulatory region of the TH gene contained in the prepared vector by sequencing at least the nucleotide sequence.

A commercially available vector may be used as the original vector for use in the present invention. For example, it is possible to prepare the vector according to the present invention, only by incorporating the transcriptional regulatory region of the TH gene prepared in (a) into a PGV-B2 vector or PGV-P2 vector (TOYO B-NET).

2. Cell

The present invention also provides a cell into which the vector is introduced. The transfected cell containing the introduced vector can be used for detection of a substance having a dioxin-, estrogen-, or androgen-like activity.

A host cell for introducing the vector according to the present invention may be any cell, preferably a mammalian cell. The kind of the mammalian cell is not particularly limited as long as the incorporated transcriptional regulatory region of TH gene can function in the cell. The mammalian cell may be, for example, a primary cultured cell or an immortalized cultured cell. That is, the mammalian cell is not particularly limited as long as the cell has at least one type of aryl hydrocarbon receptor, estrogen receptor and androgen receptor. Alternatively, at least one type of aryl hydrocarbon receptor-coding gene, estrogen receptor-coding gene and androgen receptor-coding gene may be incorporated into a mammalian cell (see Example 3 below).

Preferably, the host cell is a mammalian cell expressing an aryl hydrocarbon receptor. The mammalian cell is, for example, a human cell, mouse cell or rat cell. The "mammalian cell expressing an aryl hydrocarbon receptor" may be a mammalian cell inherently expressing the aryl hydrocarbon receptor or a gene-introduced cell that is prepared by introducing a gene coding the aryl hydrocarbon receptor into a mammalian cell.

In introducing the gene coding an aryl hydrocarbon receptor (AhR gene) into a mammalian cell, the AhR gene to be introduced may be an AhR gene derived from any mammal, for example, a human-derived AhR gene, a mouse-derived AhR gene, or a rat-derived AhR gene. A SD-line rat-derived AhR gene is shown as SEQ ID No: 10, and a C57/BL6-line mouse-derived AhR gene is shown as SEQ ID No: 11. The AhR gene may contain one or several mutations such as substitution, deletion or addition, as long as the aryl hydrocarbon receptor coded by the AhR gene can function as a ligand-dependent transcription factor.

In particular, the host cell is preferably a nerve-derived cell, in particular a cell derived from the central nervous system. The nerve-derived cell may be, for example, a human nerve-derived cell, a mouse nerve-derived cell or a rat nerve-derived cell. Specifically, for example, a neuroblastoma, in particular, mouse neuroblastoma Neuro2a, can be used. Most preferably, a gene-introduced cell that is prepared by introducing an aryl hydrocarbon receptor-coding gene into mouse neuroblastoma Neuro2a may be used as the host cell. Actually, the present inventors have been prepared a gene-introduced cell by introducing an aryl hydrocarbon receptor-coding gene of a rat into mouse neuroblastoma Neuro2a. Applicants respectfully submit that the mouse neuroblastoma Neuro2a cells were deposited on May 27, 2005 with the International Patent Organism Depositary (IPOD), National Institute of Advanced Industrial Science and Technology, AIST Tsukuba Central 6, 1-1, Higashi 1-chome, Tsukuba-shi, Ibaraki-Ken 305-8566, Japan, under the terms and conditions of the Budapest Treaty, and assigned accession numbers FERM BP-10341 and FERM BP-10342. Applicants further submit that all restrictions imposed by the depositor on the availability to the public of the deposited biological material will be irrevocably removed upon the granting of a patent on this application.

The vector according to the present invention may be incorporated into a host cell transiently or stably. For example, when the vector is incorporated transiently into a cell, mammalian cells are incubated in a container containing MEM Dulbeccos's/Ham F12 equal-volume (DF1:1) mixed medium containing 10% fetal calf serum, at 37° C. under the condition of 5% $CO_2$ for several hours to overnight. The vector according to the present invention is incorporated into the cell thus cultured. Any one of the methods known by a person skilled in the art, such as a LIPOFECTAMINE method, an electroporation method, a DEAE-dextran method, or a calcium phosphate method, may be used in introducing the vector into the cell. For example, LIPOFECTAMINE 2000 (manufactured by Invitrogen) may be used. The amount of the vector introduced, the amount of LIPOFECTAMINE 2000, the number of cells used, and the like are preferably determined in advance according to a commercially available manual. The vector to be introduced into the cell may be converted into a linear vector previously by digestion with a suitable restriction enzyme.

On the other hand, when the vector according to the present invention is incorporated stably into a cell, any method known in the art may be used. For example, a vector containing a drug-resistance gene is first prepared, and the vector containing a drug-resistance gene is incorporated into a cell similarly to the transient incorporation as described above. The cell containing the vector is then cultured in a medium containing a suitable concentration of the drug for an adequate period. After the culture, only a cell containing a drug-resistance gene, i.e., a cell into which the vector is stably introduced, results in being viable.

3. Detection Method

Hereinafter, the method of detecting a dioxin-, estrogen- or androgen-like activity of a test substance by using a cell containing the vector according to the present invention will be described in detail.

A cell containing the vector according to the present invention is first cultured in the presence or absence of a test substance (i.e., under the condition that the cell is exposed or unexposed to the test substance). The incubation period in the presence of the test substance is preferably determined in advance properly according to the type of the mammalian cell used. The incubation period is favorably a period sufficient to induce expression of the reporter gene in the presence of the test substance and detect the gene product. It would be obvious to a person skilled in the art that such incubation period varies depending on various conditions including the cell type, culture medium, culture temperature, test substance concentration, and others. Thus, it would be easy for a person skilled in the art to determine the optimal incubation period according to the conditions. The incubation period is generally about 2 hours to 3 days, and it seems possible to detect the expressed product of the reporter gene by culturing, for example, for 1 hour, 10 hours, 24 hours, or 30 hours or more.

Then, in the method according to the present invention, the amount of the expressed product of the reporter gene is measured in each cell. The expressed product can be detected by various detection methods in accordance with the type of the reporter gene used. These detection methods include, for example, a process of extracting the expressed product (protein) according to the kind of the expressed product. As the process of extracting the protein, an optimal known extraction process may be used in accordance with the kind of the reporter gene used in vector. After that, the amount of the expressed product of the reporter gene contained in the extracted proteins is measured by a method suitable for the kind of the reporter gene. The expression amount of the reporter gene in the presence of a test substance is compared with that in the absence of a test substance.

As a result, the activity of a test substance on the "enhancer region derived from the transcriptional regulatory region of the TH gene wherein the enhancer region enhances the gene transcription amount in response to the test substance" can be determined, based on the difference in the expression amount of the reporter gene between in the presence and absence of the test substance. More specifically, if the measured expression amount of the reporter gene in the cell incubated in the presence of a test substance is greater than that in the cell incubated in the absence of the test substance, it is judged that the test substance has a dioxin-, estrogen-, or androgen-like activity.

Specifically, for the purpose of detecting the estrogen- or androgen-like activity, it is preferable to use a cell carrying a vector containing the nucleotide sequence (2.5 kb) of SEQ ID No: 1, or a cell carrying a vector containing the nucleotide sequence (315 bp) of SEQ ID No: 2. For the purpose of detecting the dioxins-like activity, it is preferable to use any one of a cell carrying the nucleotide sequence (2.5 kb) of SEQ ID No: 1, a cell carrying the nucleotide sequence (315 bp) of SEQ ID No: 2, a cell carrying the nucleotide sequence (143 bp) of SEQ ID No: 3, and a cell carrying the nucleotide sequence (67 bp) of SEQ ID No: 4.

According to a favorable embodiment of the present invention, the dioxins-like activity of a test substance can be detected by using a cell carrying the nucleotide sequence (67 bp) of SEQ ID No: 4.

EXAMPLES

Example 1

Preparation of an Expression Vector Carrying an Aryl Hydrocarbon Receptor-coding Gene (a) Preparation of AhR Genes of SD-line Rat and C57/BL6-line Mouse Total RNAs were extracted from the SD-line rat brain. The extracted RNAs (template) were subjected to reverse transcription by using oligo(dT) primers. The SD-line rat AhR gene-coding region was amplified from the reverse-transcribed sample by means of PCR (25 cycles of denaturation at 94° C. for 1 minute, annealing at 55° C. for 1 minute, and elongation at 72° C. for 4 minutes) using Pyrobest DNA polymerase (Takara Bio Inc.). The following primers specific to the SD-line rat AhR gene were used. Recognition sequence for restriction enzymes HindIII (for forward primer) and recognition sequence for restriction enzymes XhoI (for reverse primer) were added to the 5'-terminal of the primers, respectively, for the purpose of facilitating incorporation of the PCR product into the vector.

```
Forward primer:
                                        (SEQ ID No: 12)
5'-CCCAAGCTTACCATGAGCAGCGGCGCCAACATCA-3'

Reverse primer:
                                        (SEQ ID No: 13)
5'-CCGCTCGAGAGGAATCCGCTGGGTGTGATATCAG-3'.
```

In addition, total RNAs were extracted from C57/BL6-line mouse liver. The extracted RNAs (template) were subjected to reverse transcription by using oligo(dT) primers. The AhR gene-coding region of the C57/BL6-line mouse was amplified from the reverse-transcribed sample by means of PCR in a reaction condition similar to that above. The following primers specific to the C57/BL6-line mouse AhR gene were used. Recognition sequence for restriction enzymes HindIII (for forward primer) and recognition sequence for restriction enzyme XbaI (for reverse primer) were added to the 5'-terminal of the primers, respectively, for the purpose of facilitating incorporation of the PCR product into the vector.

```
Forward primer:
                                        (SEQ ID No: 14)
5'-CCCAAGCTTATGAGCAGCGGCGCCAACATCACC-3'

Reverse primer:
                                        (SEQ ID No: 15)
5'-CCCTCTAGATCAACTCTGCACCTTGCTTAGGAA-3'
```

(b) Construction of AhR Gene-expressing Vector pcDNA4/V5-His B (Invitrogen) and PGV-P2 (TOYO B-Net) were used as the vectors for expression of each AhR gene prepared in (a).

The SD-line rat AhR gene, one of the AhR genes prepared in (a), was digested with restriction enzymes HindIII and XhoI and subjected to electrophoresis on 0.8% agarose. The corresponding band was excised, the gene was purified with a QIAQUICK Gel Extraction Kit (Qiagen), and incorporated into pcDNA4/V5-His B previously digested with HindIII and XhoI, to obtain a SD-line rat AhR gene-expressing vector, pcDNA4-rAhR.

The C57/BL6-line mouse AhR gene, another AhR gene prepared in (a), was digested with restriction enzymes HindIII and XbaI and subjected to electrophoresis on 0.8% agarose. The corresponding band was excised, the gene was purified with a QIAQUICK Gel Extraction Kit, and incorporated into PGV-P2 previously digested with HindIII and XbaI, to obtain a C57/BL6-line mouse AhR gene-expressing vector, PGV-mAhR.

These AhR-expressing vectors were introduced into E. coli TOP10 (manufactured by Invitrogen), and amplified and preserved therein.

The rat AhR gene incorporated into pcDNA4-rAhR and the mouse AhR gene incorporated into PGV-mAhR were found to have no mutation in the nucleotide sequence by mean of sequencing (SEQ. ID. No: 10 and 11, respectively).

Example 2

Preparation of Vector (PGV-THp25) having TH Transcriptional Regulatory Region

Approximately 2.5 kbp of a transcriptional regulatory region of tyrosine hydroxylase (TH) gene was amplified by means of PCR using a mouse genome (Clontech) previously digested with a restriction enzyme KpnI as a template (SEQ ID No: 1). Recognition sequence for restriction enzymes KpnI (for forward primer) and recognition sequence for restriction enzyme NheI (for reverse primer) were added to the 5'-terminal of the primers for PCR, respectively, in order to facilitate incorporation of the PCR product into the vector.

```
Forward primer:
                                  (SEQ ID No: 16)
5'-CGCGGTACCCTTCTCTGTGCCCACAGATGCTTTA-3'

Reverse primer:
                                  (SEQ ID No: 17)
5'-GCAGCTAGCAAGCTGGTGGTCCCGAGTTCTGTCT-3'.
```

Figure 1:
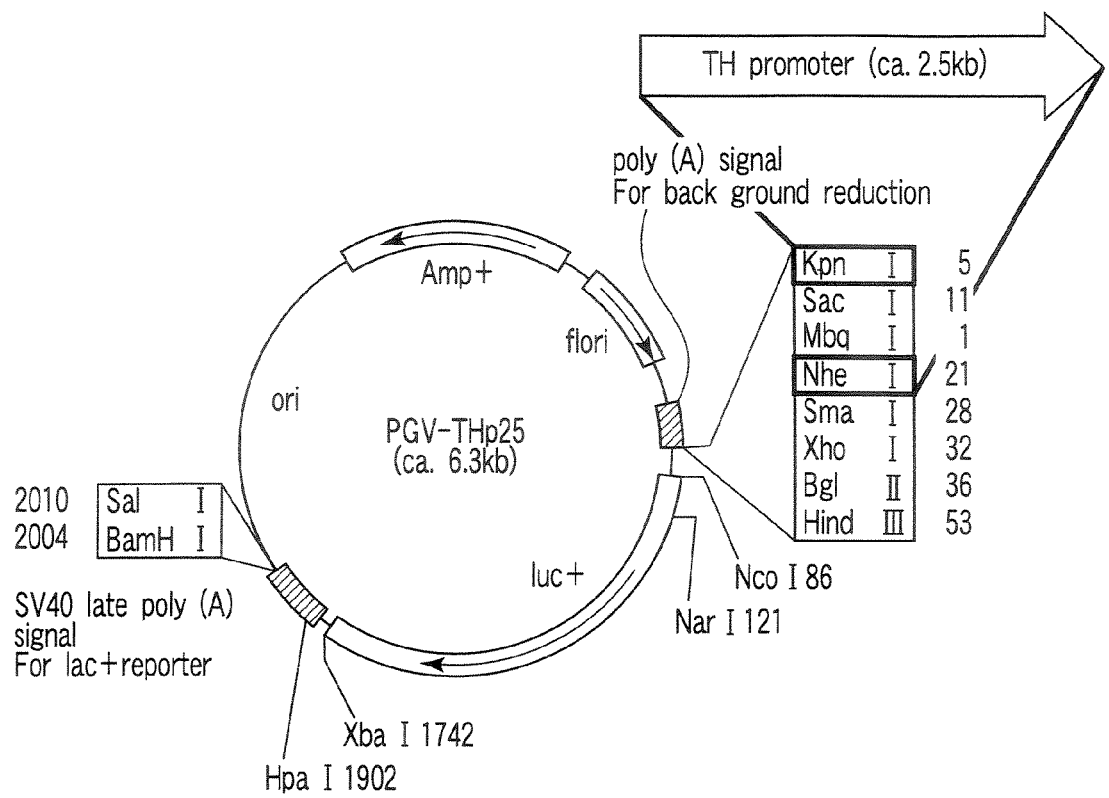
FIG. 1 is a schematic diagram illustrating a vector PGV-pTH25 according to an embodiment of the present invention.

An α type heat-stable DNA polymerase (Pyrobest DNA polymerase, Takara Bio Inc.), which has a proofreading function and has less mutation frequency during DNA replication, was used as the PCR enzyme. The TH transcriptional regulatory region amplified by PCR was digested with restriction enzymes KpnI and NheI, and subjected to electrophoresis on 0.8% agarose. The corresponding band was excised, purified with a QIAQUICK Gel Extraction Kit (manufactured by Qiagen), and incorporated into PGV-B2 vector (TOYO B-NET) previously digested with KpnI and NheI. A DNA-joining enzyme T4 DNA ligase was used for the incorporation of the TH transcriptional regulatory region into the vector. After the incorporation, the vector was introduced into an $E.$ $coli$ strain (TOP10, Invitrogen), and the $E.$ $coli$ cells are screened with an antibiotic (ampicillin), for selection of an $E.$ $coli$ strain carrying the desirable vector. The vector thus prepared was designated as PGV-THp25 (FIG. 1) and used as a vector for measurement of the action of a test substance on the transcription.

Example 3

Measurement of Activity of TCDD on Transcriptional Regulation by Using PGV-THp25-introduced Cell (Measurement of Transcription Amount of Reporter Gene after Addition of TCDD by Using PGV-THp25-introduced Cell)

In this Example, the PGV-THp25 prepared in Example 2 was used. Neuro2a was used as the cell.

Two kinds of vectors, pcDNA4-rAhR (Example 1) and pcDNA4/V5-His/lacZ (Invitrogen), were introduced into Neuro2a, together with PGV-THp25. pcDNA4-rAhR was introduced for constitutive expression of the SD-line rat AhR gene (SEQ ID No: 10) in the cell, and pcDNA4/V5-His/lacZ was introduced for normalization of the vector transfection efficiency.

The vectors were introduced into the cell by using LIPOFECTAMINE 2000 (Invitrogen). The cell was cultured on a 24-well plate, and the operation was performed according to the manual of Invitrogen. A total of 0.8 μg of vectors (0.4 μg of PGV-THp25, 0.2 μg of pcDNA4-rAhR, and 0.2 μg of pcDNA4/V5-His/lacZ) suspended in 50 μl of OPTI-MEM medium and 2 μl of LIPOFECTAMINE 2000 suspended in 50 μl of OPTI-MEM medium were mixed, and incubated at room temperature for 20 minutes to form nucleic acid/LIPOFECTAMINE 2000 complex. The obtained suspension containing the complex was added to Neuro2a cell culture, which has been previously cultured overnight in 500 μl of DF1:1 medium (containing 10% fetal calf serum) ($0.8 \times 10^5$ cells were seeded on previous day), to allow incorporation of the vectors into the cell. The cell was cultured additionally for 24 hours after the transfection, for the purpose of improvement in vector incorporation efficiency and expression of the proteins derived from the introduced vectors.

As the test substance, a solution of dioxin (2,3,7,8-tetra-chlorodibenzo-p-dioxine, TCDD) in dimethylsulfoxide (manufactured by Kanto Kagaku Co. Inc.) was used. After the transfection and the additional incubation for 24 hours, the medium was replaced with a fresh medium containing TCDD (at 0, 0.01, 1, or 100 nM), and the cell was cultured additionally for 30 hours. After 30 hours, the medium was removed from the 24-well plate, and the cell was washed with phosphate buffer twice. 100 μl of a protein extraction solution (manufactured by TOYO B-NET) was added to each well, and the cell suspension was stirred gently at room temperature for 15 minutes and then frozen at −80° C. The frozen solution was thawed at room temperature, and the resulting solution was recovered in a tube and diluted ten times with a protein extraction reagent containing 1 mg/ml bovine serum albumin. Luciferase and β-galactosidase activities in the diluted solution were measured, and the expression amount of the reporter gene was calculated as a relative luminescence intensity per 1 ng of β-galactosidase per second (RLU/sec/ng β-galactosidase).

Figure 2:
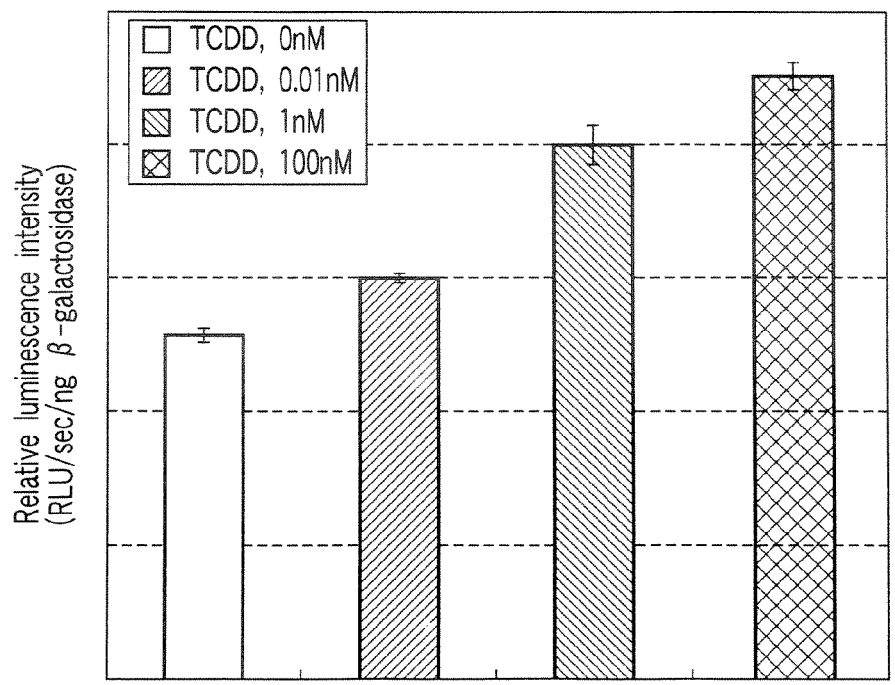
FIG. 2 is a graph showing the dose-dependent increase in the amount of a gene-product expressed after TCDD exposure in a cell containing the vector PGV-pTH25 according to an embodiment of the present invention.

As shown in FIG. 2, in the PGV-pTH25-introduced cell, the expression amount of the reporter gene increased dose-dependently on the TCDD exposure amount (approximately 1.2 times larger when exposed to 0.01 nM TCDD; approximately 1.6 times larger when exposed to 1 nM TCDD; and approximately 1.8 times larger when exposed to 100 nM TCDD). The results in FIG. 2 showed that it was possible to measure the action of TCDD on the transcriptional activity of the ligand-dependent transcription factor (i.e., aryl hydrocarbon receptor) by using the PGV-pTH25-introduced cell.

Example 4

Identification of TH Gene Transcriptional Regulatory Region (Identification of the TH Gene Transcriptional Regulatory Region having Response Property to TCDD-bound Transcription Factor)

Shorter fragments of TH transcriptional regulatory region (i.e., 2.0 kbp, 1.5 kbp, 1.0 kbp and 500 bp of fragments) were prepared by PCR using the 2.5 kbp of the TH transcriptional regulatory region incorporated into PGV-THp25 as a template. The following different forward primers were used for each fragment: 2.0-kbp fragment:

```
2.0-kbp fragment:
                                  (SEQ ID No: 18)
5'-CGCGGTACCTGGGTTTGCCTCACCCTGCAATCCC-3', 1.5-kbp fragment:
                                  (SEQ ID No: 19)
5'-CCAGGTACCGAGGTTAGGGAGTGTTCCCTTTGTA-3', 1.0-kbp fragment:
                                  (SEQ ID No: 20)
5'-CAGGGTACCGCTCAGCATAAGTCCCCTGTAGTAG-3', 500-bp fragment:
                                  (SEQ ID No: 21)
5'-CGTGGTACCACATACACTGGGGCAGTGAGTAGAT-3'.
```

As the reverse primer, a common primer (5'-GCAGCTAG-CAAGCTGGTGGTCCCGAGTTCTGTCT-3' (SEQ ID No: 17)) was used. Recognition sequence for a restriction enzyme KpnI was added to the terminal of each forward primer, and recognition sequence for a restriction enzyme NheI was added to the terminal of the reverse primer, in order to facilitate incorporation of the PCR amplification fragments into the vector. Pyrobest DNA polymerase (Takara Bio Inc.) was used in the PCR. The amplified TH transcriptional regulatory region fragments were digested with restriction enzymes KpnI and NheI, and subjected to electrophoresis on agarose. The corresponding bands were purified with a QIAQUICK Gel Extraction Kit (manufactured by Qiagen) and incorporated into PGV-B2 vector (TOYO B-NET) previously digested with KpnI and NheI.

These vectors were introduced into Neuro2a by a method similar to Example 3. The obtained cell was exposed to 10 nM TCDD, and the change in the expression amount of the reporter gene was examined in the cell (FIG. 3). The results showed that there was a response to TCDD in the cases of all vectors containing the TH transcriptional regulatory regions of 2.5 kbp to 500 bp in length. The results indicated that the region involved in transcriptional regulation by the test substance TCDD was located in the range of 0 to about 500 bp upstream of the TH gene-coding region.

For narrowing down the region involved in transcriptional regulation by the test substance, shorter fragments of the transcriptional regulatory region (i.e., 400 bp, 300 bp, 200 bp and 100 bp of fragments) were prepared by PCR using the 500 bp of the TH transcriptional regulatory region as a template. The following forward primers were used for each fragment.

```
400-bp fragment:
                                  (SEQ ID No: 22)
5'-CGGGGTACCAGATTTATTTGTCTCCAAGGGCTAT-3';

300-bp fragment:
                                  (SEQ ID No: 23)
5'-CGGGGTACCATTAGAGAGCTCTAGATGTCTCCTG-3';

200-bp fragment:
                                  (SEQ ID No: 24)
5'-CCCGGTACCCTAATGGGACGGAGGCCTCTCTCGT-3';
and 100-bp fragment:
                                  (SEQ ID No: 25)
5'-CGGGGTACCGTGGGGGACCCAGAGGGGCTTTGAC-3'.
```

As the reverse primer, a common primer (5'-GCAGCTAG-CAAGCTGGTGGTCCCGAGTTCTGTCT-3' (SEQ ID No: 17)) was used. Recognition sequence for a restriction enzyme KpnI was added to the terminal of each forward primer, and recognition sequence for a restriction enzyme NheI was added to the terminal of the reverse primer. The DNA fragments were amplified by using Pyrobest DNA polymerase (Takara Bio Inc.). The amplified TH transcriptional regulatory region fragments were digested with restriction enzymes KpnI and NheI, and subjected to electrophoresis on agarose. The corresponding bands were purified with a QIAQUICK Gel Extraction Kit (manufactured by Qiagen), and incorporated into PGV-B2 vector (TOYO B-NET) previously digested with KpnI and NheI.

The prepared vectors were introduced into Neuro2a by a method similar to the above case of the vectors containing 2.5 kbp to 500 bp fragments. The obtained cell was exposed to 10 nM TCDD, and the change in the expression amount of the reporter gene was examined. As shown in FIG. 4, there was a response to TCDD in the cases of the vectors containing the TH transcriptional regulatory region of 500 bp, 400 bp, or 300 bp in length, but there was no response to TCDD in the cases of the vectors containing the region of 200 bp or 100 bp. The results indicated that the upstream region (SEQ ID No: 2) located in approximately 300 to 200 bp upstream of the coding region was involved in the transcriptional regulation of the TH gene in response to the test substance.

Example 5

Measurement of Activity of Test Substance on Transcriptional Regulation (Measurement of Transcription Amount of Reporter Gene after Addition of Test Substance by Using PGH-THp03-introduced Cell)

The TH transcriptional regulatory region of SEQ ID No: 2 was used in Example 5.

A vector (PGV-THp03) containing the upstream region (SEQ ID No: 2) ranging from about −300 to 0 position of the TH gene-coding region, which was prepared in Example 4, was used. Neuro2a was used as the cell.

Two kinds of vectors, pcDNA4-rAhR (Example 1) and pcDNA4/V5-His/lacZ (Invitrogen), were introduced into Neuro2a, together with PGV-THp03. pcDNA4-rAhR was introduced for constitutive expression of the SD-line rat AhR gene (SEQ ID No: 10) in the cell, and pcDNA4/V5-His/lacZ was introduced for normalization of the vector transfection efficiency.

The vectors were introduced into the cell by using LIPO-FECTAMINE 2000 (Invitrogen). The cell was cultured on a 24-well plate, and the operation was performed according to the manual of Invitrogen. A total of 0.8 μm of vectors (0.4 μg of PGV-THp03, 0.2 μg of pcDNA4-rAhR, and 0.2 μg of pcDNA4/V5-His/lacZ) suspended in 50 μl of OPTI-MEM medium and 2 μl of LIPOFECTAMINE 2000 suspended in 50 μl of OPTI-MEM medium were mixed, and incubated at room temperature for 20 minutes to form nucleic acid/LIPO-FECTAMINE 2000 complex. The obtained suspension containing the complex was added to Neuro2a cell culture, which has been previously cultured overnight in 500 μl of DF1:1 medium (containing 10% fetal calf serum) ($0.8 \times 10^5$ cells were seeded on previous day), to allow incorporation of the vectors into the cell. The cell was cultured additionally for 24 hours after transfection, for the purpose of improvement in vector incorporation efficiency and expression of the protein derived from the introduced vectors.

As the test substances, vinclozolin (10 μM), dimethyl phthalate (10 μM), benzopyrene (1 μM), and dioxin (TCDD) (10 nM) were used. After the transfection and the additional incubation for 24 hours, the medium was replaced with a fresh medium containing any one of the test substances, and the cell was cultured additionally for 30 hours. After 30 hours, the medium was removed from the 24-well plate, and the cell was washed with phosphate buffer twice. 100 μl of a protein extraction solution (manufactured by TOYO B-NET) was added to each well, and the cell suspension was stirred gently at room temperature for 15 minutes and then frozen at −80° C. The frozen solution was thawed at room temperature, and the resulting solution was recovered in a tube and diluted ten times with a protein extraction reagent containing 1 mg/ml bovine serum albumin luciferase and β-galactosidase activities in the diluted solution were measured, and the expression amount of the reporter gene was calculated as a relative luminescence intensity per 1 ng of β-galactosidase per second (RLU/sec/ng β-galactosidase).

The results are summarized in FIG. 5. Dioxin and benzopyrene are known to bind to aryl hydrocarbon receptor (AhR) and activate the receptor. Dioxin increased the luciferase activity approximately 1.4 times (FIG. 5(A)), and benzopyrene increased the luciferase activity approximately 1.3 times (FIG. 5(B)). In addition, vinclozolin, which is known to bind to androgen receptor (AR), also increased the luciferase activity approximately 1.3 times in the AhR-introduced cell (FIG. 5(C)). On the other hand, there was no change in luciferase activity in the cell with no AhR introduced. Dimethyl phthalate, which is known to bind to estrogen receptor (ER), showed an increase of luciferase activity by approximately 1.2 times (FIG. 5(D)). This Example demonstrated that it was possible to measure the action of test substances on the transcriptional activity of at least 3 kinds of ligand-dependent transcription factors (AhR, ER, and AR) in the PGV-pTH03-introduced cell.

Example 6

Measurement of Activity of Test Substance on Transcriptional Regulation, by Using TH Transcriptional Regulatory Region (−300 to −200 bp)

The TH transcriptional regulatory region of SEQ ID No: 3 (−300 to −200 bp) was used in Example 6. The TH transcriptional regulatory region ranging from −300 to −200 position was prepared by PCR using the 500-bp size of TH transcriptional regulatory region as a template. The following primers were used.

```
Forward primer:
                                         (SEQ ID No: 23)
5'-CGGGGTACCATTAGAGAGCTCTAGATGTCTCCTG-3';
and Reverse primer:
                                         (SEQ ID No: 26)
5'-GCCGCTAGCACGAGAGAGGCCTCCGTCCCATTAG-3'.
```

Recognition sequences for restriction enzymes KpnI (for forward primer) and NheI (for reverse primer) were added to the terminal of the respective primers, for the purpose of facilitating incorporation of the PCR amplified fragment into the vector. The region of SEQ ID No: 3 was amplified by using Pyrobest DNA polymerase. The amplified DNA fragment was digested with restriction enzymes KpnI and NheI, and subjected to electrophoresis on agarose. The corresponding band was purified with a QIAQUICK Gel Extraction Kit, and incorporated into PGV-P2 vector previously digested with KpnI and NheI, to obtain a recombinant vector pSV40E100/Luc. The vector PGV-P2 used contains an SV40 early promoter as its promoter region.

In addition, the region of SEQ ID No: 5 (mouse TH gene core promoter region) was amplified by PCR using a forward primer: 5'-CGGCTCGAGGTGGGGGACCCA-GAGGGGCTTTGAC-3' (SEQ ID No: 27) and a reverse primer: 5'-GCAAAGCTTAAGCTGGTGGTCCCGAGT-TCTGTCT-3' (SEQ ID No: 28), and using a region of approximately 500 by upstream of the TH gene as the template. The amplified DNA was digested with XhoI and HindIII, and subjected to 0.8% agarose gel electrophoresis. The corresponding DNA fragment was excised from the gel, and purified with a QIAQUICK Gel Extraction Kit. The purified fragment having nucleotide sequence of SEQ ID No: 5 was digested similarly with XhoI and HindIII, and incorporated into a vector PGV-P2 containing no SV40 early promoter with a ligation kit (Toyobo), to obtain a recombinant vector pTHE100/Luc.

These vectors (pSV40E100/Luc and pTHE100/Luc) were introduced into *E. coli* TOP10 strain (Invitrogen), and amplified and preserved therein.

The two kinds of vectors thus prepared (containing a TH transcriptional regulatory region of SEQ ID No: 3, a promoter, and a reporter gene) are shown in FIG. 6A. The vector prepared was introduced into Neuro2a by a method similar to Example 3. The obtained cell was exposed to 10 nM TCDD, and the change in the expression amount of the reporter gene was examined. The results showed that it was possible to measure the action of the test substance on transcriptional regulation by incorporating the TH transcriptional regulatory region (SEQ ID No: 3) into the vector (FIG. 6B). It was also shown that the combination the region of SEQ ID No: 3 and the TH gene core promoter showed higher activity in response to a test substance than that of the combination of the region of SEQ ID No: 3 and the SV40 early promoter (FIG. 6B).

Example 7

Figures 7A, 7B:
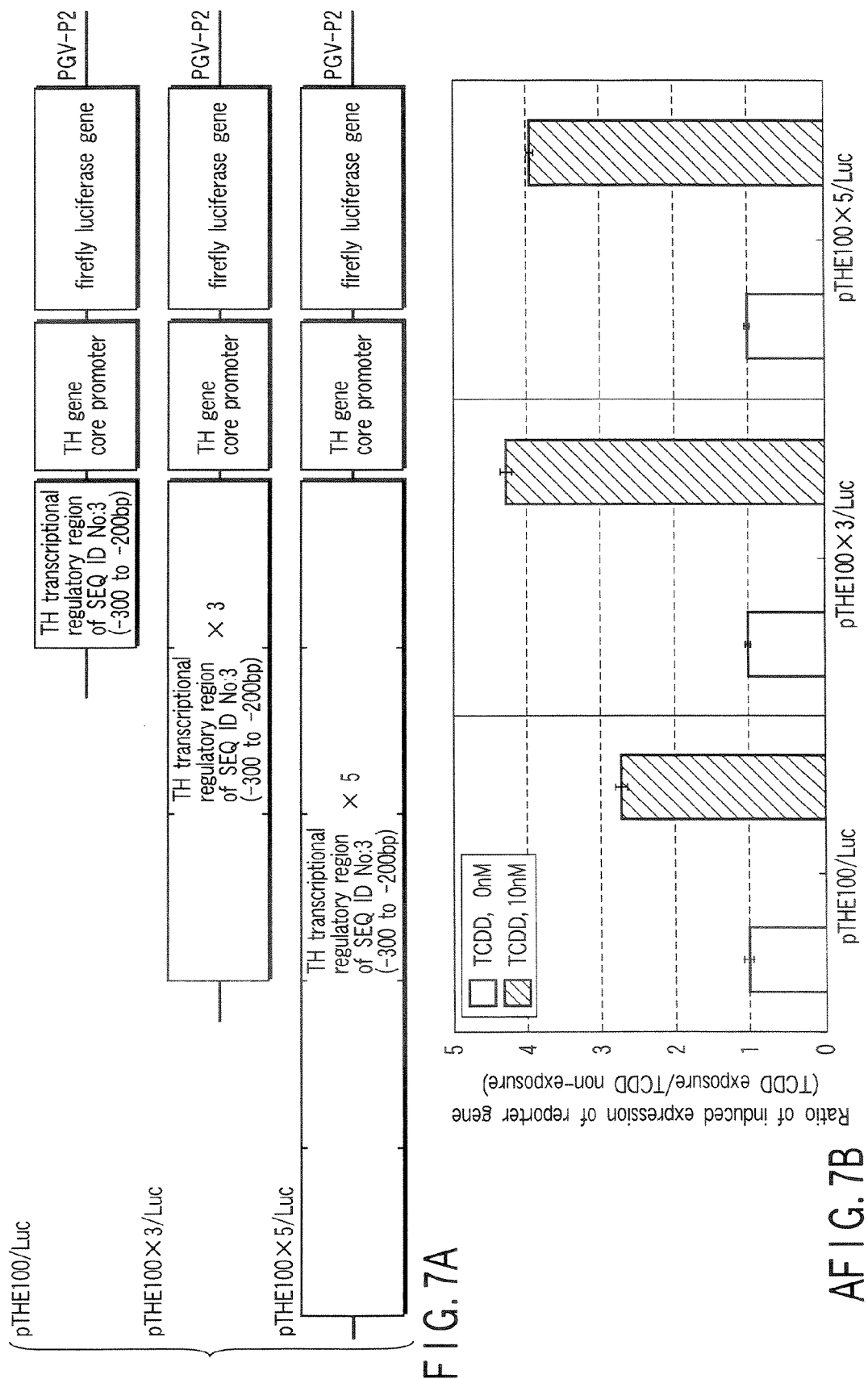
FIG. 7A is a schematic diagram illustrating vectors pTHE100×3/LUC and pTHE100×5/LUC according to an embodiment of the present invention containing tandem repeats of the TH transcriptional regulatory region of SEQ ID No: 3.
FIG. 7B is a graph showing the amounts of the reporter gene-product expressed by the vectors in the presence of a test substance TCDD.

Preparation of Vector Containing Multiple Copies of the Region of SEQ ID No: 3 and Measurement of Activity of Test Substance on Transcriptional Regulation by Using the Vector The terminal of the "region of SEQ ID No: 3 amplified by PCR in Example 6" was phosphorylated with 5'-polynucleotide kinase (Takara Bio Inc.), and then, the regions of SEQ ID No: 3 were ligated in tandem with each other by using a ligation kit (Toyobo). The ligated DNA fragment was digested with restriction enzymes KpnI and NheI, and subjected to agarose gel electrophoresis. DNA fragment consisting of three copies of the regions of SEQ ID No: 3 linked in tandem and DNA fragment consisting of five copies of the regions of SEQ ID No: 3 linked in tandem were excised from the gel based on their molecular weight, and purified with a QIAQUICK Gel Extraction Kit. These DNA fragments were digested with KpnI and NheI, and incorporated into a vector pTHE100/Luc containing no region of SEQ ID No: 3, to prepare a recombinant vector pTHE100×3/Luc containing three tandem copies of the regions of SEQ ID No: 3, and a recombinant vector pTHE100×5/Luc containing five tandem copies of the regions of SEQ ID No: 3 (FIG. 7A). pTH100/Luc, pTHE100×3/Luc, and pTHE100×5/Luc were introduced into Neuro2a by a method similar to that in Example 3. The obtained cell was exposed to 10 nM TCDD, and then, the change in the expression amount of the reporter gene was examined (FIG. 7B). The result showed that the incorporation of multiple copies of the regions of SEQ ID No: 3 into a vector was effective in increasing the activity of the test substance on transcriptional regulation. In addition, the increase in the activity of the test substance on transcriptional regulation was highest with the vector pTHE100×3/Luc containing three copies of the regions of SEQ ID No: 3.

Further, the transcriptional response to the TCDD concentration and the transcriptional response to dioxin congeners were evaluated by using the pTHE100×3/Luc. The transcriptional response to the TCDD concentration was determined by a method similar to that in Example 3, specifically, by incorporating the vector pTHE100×3/Luc into Neuro2a, exposing the obtained cell to 1 to 10,000 μM of TCDD, and measuring the change in the expression amount of the reporter gene. The result showed that the expression amount of the reporter gene increased statistically significantly with the increase in TCDD concentration up to 10 μM (FIG. 8A). On the other hand, the transcriptional response to dioxin congeners was determined by a method similar to that in Example 3, specifically, by incorporating the vector pTHE100×3/Luc into Neuro2a, exposing the obtained cell to eight kinds of dioxin congeners including TCDD, and measuring the activity of these congeners on transcriptional regulation. The eight kinds of dioxin congeners used are as follows:
1-monochloro-dibenzo-p-dioxin (1-MCDD);
2,7-dichloro-dibenzo-p-dioxin (2,7-DCDD);
1,2,3-trichloro-dibenzo-p-dioxin (1,2,3-TrCDD);
2,3,7,8-tetrachloro-dibenzo-p-dioxin (2,3,7,8-TCDD);
1,2,3,7,8-pentachloro-dibenzo-p-dioxin (1,2,3,7,8-PeCDD);
1,2,3,4,7,9-hexachloro-dibenzo-p-dioxin (1,2,3,7,9-HxDD);
1,2,3,4,6,7,8-heptachloro-dibenzo-p-dioxin (1,2,3,4,6,7,8-HpCDD); and
1,2,3,4,6,7,8,9-octachloro-dibenzo-p-dioxin (OCDD).

The result showed that five kinds of dioxin congeners including TCDD exerted influence on transcriptional regulation (FIG. 8B).

Example 8

Effect of the Kind of AhR Gene (SD-line Rat AhR Gene or C57/BL6-line Mouse AhR Gene) on Activity of Test Substance on Transcriptional Regulation In Example 8, the vector pTHE100×3/Luc (Example 7, FIG. 7A) was used as the vector containing a reporter gene, and Neuro2a was used as the cell.

In this Example, a combination of pcDNA4-rAhR (Example 1) containing the SD-line rat AhR gene and pcDNA4/V5-His/lacZ (Invitrogen), as well as a combination of PGV-mAhR (Example 1) containing the C57/BL6-line mouse AhR gene and pcDNA4/V5-His/lacZ were used as the vectors for introducing into the cell together with pTHE100×3/Luc. pcDNA4-rAhR was introduced into the cell for constitutive expression of the SD-line rat AhR (SEQ ID No: 10); PGV-mAhR was introduced into the cell for constitutive expression of C57/BL6-line mouse AhR (SEQ ID No: 11); and pcDNA4/V5-His/lacZ was introduced into the cell for normalization of the transfection efficiency of the vector.

Figure 9:
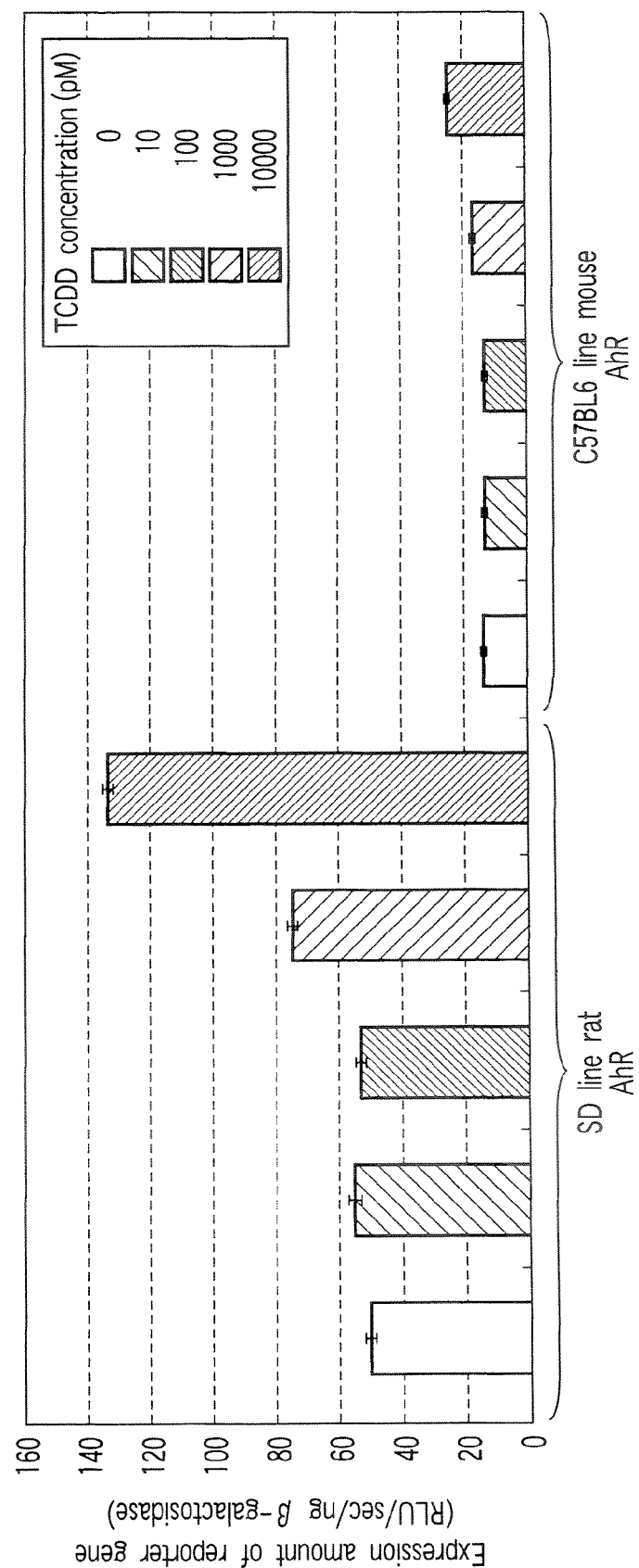
FIG. 9 is a graph showing the influence of two kinds of AhR's (SD-line rat AhR and C57/BL6-line mouse AhR) on the transcriptional regulation of the vector pTHE100×3 according to an embodiment of the present invention.

The vectors were introduced into the cell by using LIPOFECTAMINE 2000, similarly to the method described in Example 3. After the above vectors were introduced into the cell, the obtained cell was exposed to 1 to 10,000 pM of TCDD to examine the increase in expression amount of the reporter gene in response to TCDD. The results showed that both AhR's (rat and mouse AhR's) were effective in inducing transcription of the reporter gene in response to TCDD, but the SD-line rat AhR gene induced a transcriptional response greater than that of the C57/BL6-line mouse AhR (FIG. 9).

Example 9

Further Screening of TCDD-responsive Region in Region of SEQ ID No: 3, and Measurement of Activity of Test Substance on Transcriptional Regulation by Using Vector Containing the Responsive Region In Example 9, the region of SEQ ID No: 4 was used as the TCDD-responsive region in the TH transcriptional regulatory region. The region of SEQ ID No: 4 was amplified by PCR using the region of SEQ ID No: 3 as a template and using the following primers: Forward primer: 5'-AGCGGTACCCT-GTCTTCATGTCGTGTCTAGG-3' (SEQ ID No: 29); and Reverse primer: 5'-AGCGCTAGCTGCATCCACTGTCG-CAGGCACC-3' (SEQ ID No: 30). Pyrobest DNA polymerase was used in the PCR. Recognition sequences for restriction enzymes KpnI (for forward primer) and NheI (for reverse primer) were added to the terminal of the respective primers, for the purpose of facilitating incorporation of the PCR amplified fragment into the vector. The terminal of the region of SEQ ID No: 4 amplified by PCR was phosphorylated with 5'-polynucleotide kinase (Takara Bio Inc.), and then, the regions of SEQ ID No: 4 were ligated in tandem with each other by using a ligation kit. The ligated DNA fragments were digested with restriction enzymes KpnI and NheI, and subjected to agarose gel electrophoresis. DNA fragment consisting of a single copy of the region of SEQ ID No: 4 and DNA fragment consisting of three copies of the regions of SEQ ID No: 4 linked in tandem were excised from the gel based on their molecular weight, and purified with a QIAQUICK Gel Extraction Kit. These DNA fragments were digested with KpnI and NheI, and incorporated into a vector pTHE100/Luc containing no region of SEQ ID No: 3, to prepare a recombinant vector pTHE60/Luc containing a single copy of the region of SEQ ID No: 4, and a recombinant vector pTHE60×3/Luc containing three tandem copies of the regions of SEQ ID No: 4 (FIG. 10A).

The vectors thus prepared were introduced into Neuro2a by a method similar to that in Example 3. The obtained cell was exposed to TCDD at concentrations of 1 nM and 10 nM, and then, the change in the expression amount of the reporter gene was examined (FIG. 10B). The results showed that it was possible to measure the activity of the test substance on transcriptional regulation by using the recombinant vectors containing the region of SEQ ID No: 4. It was also shown that the activity of the test substance increased according to the increase in the number of the regions incorporated into the vector.

What is claimed is:

1. A vector comprising:
    an enhancer region from a transcriptional regulatory region of tyrosine hydroxylase gene, wherein the enhancer region is a region consisting of tandem repeats of the nucleotide sequence of SEQ ID No: 4 and wherein the enhancer region enhances transcription amount of a functionally linked downstream gene in response to a test substance;
    a promoter which is functionally linked to downstream of the enhancer region; and
    a reporter gene which is functionally linked to downstream of the promoter.

2. The vector according to claim 1, wherein the promoter is selected from the group consisting of SEQ ID No: 5, SEQ ID No: 6, SEQ ID No: 7, SEQ ID No: 8 and SEQ ID No: 9.

3. The vector according to claim 1, wherein the reporter gene is selected from the group consisting of luciferase gene, green fluorescent protein gene, chloramphemicol acetyl transferase gene, and β-galactosidase gene.

4. A kit for detecting dioxin-like activity of a test substance, comprising the vector according to claim 1.

5. The kit according to claim 4, wherein the promoter is selected from the group consisting of SEQ ID No: 5, SEQ ID No: 6, SEQ ID No: 7, SEQ ID No: 8 and SEQ ID No: 9.

6. The kit according to claim 4, wherein the reporter gene is selected from the group consisting of luciferase gene, green fluorescent protein gene, chloramphemicol acetyl transferase gene, and β-galactosidase gene.

7. A vector comprising:
    an enhancer region from a transcriptional regulatory region of tyrosine hydroxylase gene, wherein the enhancer region is a region consisting of tandem repeats of the nucleotide sequence of SEQ ID No: 3 and wherein the enhancer region enhances transcription amount of a functionally linked downstream gene in response to a test substance;
    a promoter which is functionally linked to downstream of the enhancer region; and
    a reporter gene which is functionally linked to downstream of the promoter.

8. The vector according to claim 7, wherein the promoter is selected from the group consisting of SEQ ID No: 5, SEQ ID No: 6, SEQ ID No: 7, SEQ ID No: 8 and SEQ ID No: 9.

9. The vector according to claim 7, wherein the reporter gene is selected from the group consisting of luciferase gene, green fluorescent protein gene, chloramphemicol acetyl transferase gene, and β-galactosidase gene.

10. A kit for detecting dioxin-like activity of a test substance, comprising the vector according to claim 7.

11. The kit according to claim 10, wherein the promoter is selected from the group consisting of SEQ ID No: 5, SEQ ID No: 6, SEQ ID No: 7, SEQ ID No: 8 and SEQ ID No: 9.

12. The kit according to claim 10, wherein the reporter gene is selected from the group consisting of luciferase gene, green fluorescent protein gene, chloramphemicol acetyl transferase gene, and β-galactosidase gene.

13. A transfected mammalian cell wherein a vector comprising the following (i) to (iii) is introduced into a mammalian cell expressing an aryl hydrocarbon receptor:
    (i) an enhancer region from a transcriptional regulatory region of tyrosine hydroxylase gene, wherein the enhancer region comprises the nucleotide sequence of SEQ ID No: 4 and wherein the enhancer region enhances transcription amount of a functionally linked downstream gene in response to a test substance;
    (ii) a promoter which is functionally linked to downstream of the enhancer region; and
    (iii) a reporter gene which is functionally linked to downstream of the promoter,
    wherein the mammalian cell expressing an aryl hydrocarbon receptor is a gene-introduced cell designated as Accession Number FERM BP-10341 or FERM BP-10342 which was prepared by introducing an aryl hydrocarbon receptor-coding gene of a rat into mouse neuroblastoma Neuro 2a.

14. The transfected mammalian cell according to claim 13, wherein the enhancer region is a region consisting of tandem repeats of the nucleotide sequence of SEQ ID No: 3.

15. The transfected mammalian cell according to claim 14, wherein the promoter is selected from the group consisting of SEQ ID No: 5, SEQ ID No: 6, SEQ ID No: 7, SEQ ID No: 8 and SEQ ID No: 9.

16. The transfected mammalian cell according to claim 13, wherein the enhancer region is a region consisting of tandem repeats of the nucleotide sequence of SEQ ID No: 4.

17. The transfected mammalian cell according to claim 16, wherein the promoter is mouse selected from the group consisting of SEQ ID No: 5, SEQ ID No: 6, SEQ ID No: 7, SEQ ID No: 8 and SEQ ID No: 9.

18. The transfected mammalian cell according to claim 13, wherein the reporter gene is selected from the group consisting of luciferase gene, green fluorescent protein gene, chloramphemicol acetyl transferase gene, and β-galactosidase gene.

19. A kit for detecting dioxin-like activity of a test substance, comprising the transfected mammalian cell according to claim 13.

20. The kit according to claim 19, wherein the enhancer region is a region consisting of tandem repeats of the nucleotide sequence of SEQ ID No: 3 and wherein the kit is used for detecting dioxin-like activity of a test substance.

21. The kit according to claim 20, wherein the promoter is selected from the group consisting of SEQ ID No: 5, SEQ ID No: 6, SEQ ID No: 7, SEQ ID No: 8 and SEQ ID No: 9.

22. The kit according to claim 19, wherein the enhancer region is a region consisting of tandem repeats of the nucleotide sequence of SEQ ID No: 4 and wherein the kit is used for detecting dioxin-like activity of a test substance.

23. The kit according to claim 22, wherein the promoter is selected from the group consisting of SEQ ID No: 5, SEQ ID No: 6, SEQ ID No: 7, SEQ ID No: 8 and SEQ ID No: 9.

24. The kit according to claim 19, wherein the reporter gene is selected from the group consisting of luciferase gene, green fluorescent protein gene, chloramphemicol acetyl transferase gene, and β-galactosidase gene.

25. A transfected isolated mammalian cell wherein a vector comprising the following (i) to (iii) is introduced into a mammalian cell expressing an aryl hydrocarbon receptor:
    (i) an enhancer region from a transcriptional regulatory region of tyrosine hydroxylase gene, wherein the enhancer region comprises the nucleotide sequence of SEQ ID No: 4 and wherein the enhancer region enhances transcription amount of a functionally linked downstream gene in response to a test substance;
    (ii) a promoter which is functionally linked to downstream of the enhancer region; and
    (iii) a reporter gene which is functionally linked to downstream of the promoter, wherein the mammalian cell expressing an aryl hydrocarbon receptor is a gene-introduced cell which is prepared by introducing an aryl hydrocarbon receptor-coding gene into a mammalian cell.

26. The transfected mammalian cell according to claim 25, wherein the enhancer region is a region consisting of tandem repeats of the nucleotide sequence of SEQ ID No: 3.

27. The transfected mammalian cell according to claim 26, wherein the promoter is selected from the group consisting of SEQ ID No: 5, SEQ ID No: 6, SEQ ID No: 7, SEQ ID No: 8 and SEQ ID No: 9.

28. The transfected mammalian cell according to claim 25, wherein the enhancer region is a region consisting of tandem repeats of the nucleotide sequence of SEQ ID No: 4.

29. The transfected mammalian cell according to claim 28, wherein the promoter is selected from the group consisting of SEQ ID No: 5, SEQ ID No: 6, SEQ ID No: 7, SEQ ID No: 8 and SEQ ID No: 9.

30. The transfected mammalian cell according to claim 25, wherein the reporter gene is selected from the group consisting of luciferase gene, green fluorescent protein gene, chloramphemicol acetyl transferase gene, and β-galactosidase gene.

31. A kit for detecting dioxin-like activity of a test substance, comprising the transfected mammalian cell according to claim 25.

32. The kit according to claim 31, wherein the enhancer region is a region consisting of tandem repeats of the nucleotide sequence of SEQ ID No: 3 and wherein the kit is used for detecting dioxin-like activity of a test substance.

33. The kit according to claim 32, wherein the promoter is selected from the group consisting of SEQ ID No: 5, SEQ ID No: 6, SEQ ID No: 7, SEQ ID No: 8 and SEQ ID No: 9.

34. The kit according to claim 31, wherein the enhancer region is a region consisting of tandem repeats of the nucleotide sequence of SEQ ID No: 4 and wherein the kit is used for detecting dioxin-like activity of a test substance.

35. The kit according to claim 34, wherein the promoter is selected from the group consisting of SEQ ID No: 5, SEQ ID No: 6, SEQ ID No: 7, SEQ ID No: 8 and SEQ ID No: 9.

36. The kit according to claim 31, wherein the reporter gene is selected from the group consisting of luciferase gene, green fluorescent protein gene, chloramphemicol acetyl transferase gene, and β-galactosidase gene.

37. A method for detecting dioxin-like activity of a test substance, comprising:
(1) culturing a cell into which a vector comprising the following (i) to (iii) is introduced, in the presence of a test substance and in the absence of the test substance, respectively:
  (i) an enhancer region from a transcriptional regulatory region of tyrosine hydroxylase gene, wherein the enhancer region is a region consisting of the nucleotide sequence of SEQ ID No: 4 and wherein the enhancer region enhances transcription amount of a functionally linked downstream gene in response to a test substance;
  (ii) a promoter which is functionally linked to downstream of the enhancer region; and
  (iii) a reporter gene which is functionally linked to downstream of the promoter;
(2) determining the expression amount of the reporter gene in the cell after said culturing; and
(3) evaluating that the test substance has dioxin-like activity, in the case where the determined value of the expression amount of the reporter gene in the cell cultured in the presence of the test substance is higher than that in the cell cultured in the absence of the test substance.

38. The method according to claim 37, wherein the promoter is selected from the group consisting of SEQ ID No: 5, SEQ ID No: 6, SEQ ID No: 7, SEQ ID No: 8 and SEQ ID No: 9.

39. The method according to claim 37, wherein the reporter gene is selected from the group consisting of luciferase gene, green fluorescent protein gene, chloramphemicol acetyl transferase gene, and β-galactosidase gene.

40. A method for detecting dioxin-like activity of a test substance, comprising:
(1) culturing a cell into which a vector comprising the following (i) to (iii) is introduced, in the presence of a test substance and in the absence of the test substance, respectively:
  (i) an enhancer region from a transcriptional regulatory region of tyrosine hydroxylase gene, wherein the enhancer region is a region consisting of the nucleotide sequence of SEQ ID No: 3 and wherein the enhancer region enhances transcription amount of a functionally linked downstream gene in response to a test substance;
  (ii) a promoter which is functionally linked to downstream of the enhancer region; and
  (iii) a reporter gene which is functionally linked to downstream of the promoter;
(2) determining the expression amount of the reporter gene in the cell after said culturing; and
(3) evaluating that the test substance has dioxin-like activity, in the case where the determined value of the expression amount of the reporter gene in the cell cultured in the presence of the test substance is higher than that in the cell cultured in the absence of the test substance.

41. The method according to claim 40, wherein the promoter is selected from the group consisting of SEQ ID No: 5, SEQ ID No: 6, SEQ ID No: 7, SEQ ID No: 8 and SEQ ID No: 9.

42. The method according to claim 40, wherein the reporter gene is selected from the group consisting of luciferase gene, green fluorescent protein gene, chloramphemicol acetyl transferase gene, and β-galactosidase gene.

43. A method for detecting dioxin-like activity of a test substance, comprising:
(1) culturing a cell into which the vector according to claim 7 is introduced, in the presence of a test substance and in the absence of the test substance, respectively;
(2) determining the expression amount of the reporter gene in the cell after said culturing; and
(3) evaluating that the test substance has dioxin-like activity, in the case where the determined value of the expression amount of the reporter gene in the cell cultured in the presence of the test substance is higher than that in the cell cultured in the absence of the test substance.

44. The method according to claim 43, wherein the promoter is selected from the group consisting of SEQ ID No: 5, SEQ ID No: 6, SEQ ID No: 7, SEQ ID No: 8 and SEQ ID No: 9.

45. The method according to claim 43, wherein the reporter gene is selected from the group consisting of luciferase gene, green fluorescent protein gene, chloramphemicol acetyl transferase gene, and β-galactosidase gene.

46. A method for detecting dioxin-like activity of a test substance, comprising:
(1) culturing a cell into which the vector according to claim 1 is introduced, in the presence of a test substance and in the absence of the test substance, respectively;
(2) determining the expression amount of the reporter gene in the cell after said culturing; and (3) evaluating that the test substance has dioxin-like activity, in the case where the determined value of the expression amount of the reporter gene in the cell cultured in the presence of the test substance is higher than that in the cell cultured in the absence of the test substance.

47. The method according to claim 46, wherein the promoter is selected from the group consisting of SEQ ID No: 5, SEQ ID No: 6, SEQ ID No: 7, SEQ ID No: 8 and SEQ ID No: 9.

48. The method according to claim 46, wherein the reporter gene is selected from the group consisting of luciferase gene, green fluorescent protein gene, chloramphemicol acetyl transferase gene, and β-galactosidase gene.

49. A method for detecting dioxin-like activity of a test substance, comprising:
(1) culturing the transfected mammalian cell according to claim 13, in the presence of a test substance and in the absence of the test substance, respectively;
(2) determining the expression amount of the reporter gene in the cell after said culturing; and
(3) evaluating that the test substance has dioxin-like activity in the case where the determined value of the expression amount of the reporter gene in the cell cultured in the presence of the test substance is higher than that in the cell cultured in the absence of the test substance.

50. The method according to claim 49, wherein the enhancer region is a region consisting of tandem repeats of the nucleotide sequence of SEQ ID No: 3 and wherein the method is used for detecting dioxin-like activity of a test substance.

51. The method according to claim 50, wherein the promoter is selected from the group consisting of SEQ ID No: 5, SEQ ID No: 6, SEQ ID No: 7, SEQ ID No: 8 and SEQ ID No: 9.

52. The method according to claim 49, wherein the enhancer region is a region consisting of tandem repeats of the nucleotide sequence of SEQ ID No: 4 and wherein the method is used for detecting dioxin-like activity of a test substance.

53. The method according to claim 52, wherein the promoter is selected from the group consisting of SEQ ID No: 5, SEQ ID No: 6, SEQ ID No: 7, SEQ ID No: 8 and SEQ ID No: 9.

54. The method according to claim 49, wherein the reporter gene is selected from the group consisting of luciferase gene, green fluorescent protein gene, chloramphemicol acetyl transferase gene, and β-galactosidase gene.

55. A method for detecting dioxin-like activity of a test substance, comprising:
(1) culturing the transfected mammalian cell according to claim 25, in the presence of a test substance and in the absence of the test substance, respectively;
(2) determining the expression amount of the reporter gene in the cell after said culturing; and
(3) evaluating that the test substance has dioxin-like activity in the case where the determined value of the expression amount of the reporter gene in the cell cultured in the presence of the test substance is higher than that in the cell cultured in the absence of the test substance.

56. The method according to claim 55, wherein the enhancer region is a region consisting of tandem repeats of the nucleotide sequence of SEQ ID No: 3 and wherein the method is used for detecting dioxin-like activity of a test substance.

57. The method according to claim 56, wherein the promoter is selected from the group consisting of SEQ ID No: 5, SEQ ID No: 6, SEQ ID No: 7, SEQ ID No: 8 and SEQ ID No: 9.

58. The method according to claim 55, wherein the enhancer region is a region consisting of tandem repeats of the nucleotide sequence of SEQ ID No: 4 and wherein the method is used for detecting dioxin-like activity of a test substance.

59. The method according to claim 58, wherein the promoter is selected from the group consisting of SEQ ID No: 5, SEQ ID No: 6, SEQ ID No: 7, SEQ ID No: 8 and SEQ ID No: 9.

60. The method according to claim 55, wherein the reporter gene is selected from the group consisting of luciferase gene, green fluorescent protein gene, chloramphemicol acetyl transferase gene, and β-galactosidase gene.

* * * * *

SEQUENCE LISTING

```
<160> NUMBER OF SEQ ID NOS: 32

<210> SEQ ID NO 1
<211> LENGTH: 2500
<212> TYPE: DNA
<213> ORGANISM: Mus musculus

<400> SEQUENCE: 1
agggcttctc tgtgcccaca gatgctttag atcttggcac agtgtggtct accagctgtc      60
tctctctgtg tatatatatg tatttcatag acagtgtaca gtggcctggt ttgtgctatc     120
aggctggata tggacagagg caagagtttg tggcagcagt tatctcccaa gagagtccaa     180
agacatcatg ttttcaagtt taggccaggt gctacttgag agagctcaga cacagacaaa     240
```

-continued

```
ggtctggaga gcacatgtcc tccacccca cctagcttct gttgcaagca cctccagccg    300
agacaagaga acgaattaaa aagcaatatt tgtgtcagtg taagacattt gccgaaaggt    360
taaatccaca ttcgtgttgc tgcagagcag cccctatgc aggatttgtt agatacagct    420
ccgtcctacc ctgtgccagc tgagcaaacg ccaggctggg tggggtggaa cccagcctgg    480
gtttgcctca ccctgcaatc cccccagcac cctctaaagg aggaccctgt ggtgggcatg    540
cagacctagg gactgggcat agataacctt tgggtttggg caacagcccc cactcctcag    600
gattgaaggc taaggtgcag ccagctctgc cttcatggtg ggaatgtctc cacgtgaccc    660
ctttctgggc tgtggagaac actcagagaa gagtcctggg atgccaggca ggccagggat    720
gtgctgggca tgttgagaca ggagtgggct aagccagcag agttgctgac ccaggaagag    780
ttcagaaagg ggcatggaac atggggaggg gtccatagtg agagagagca ggcagtgcag    840
agtaaatagt ccctgagctg ggggttatgg gatttgcagg agcttgctca gagaaggcag    900
aggagagatg ctgcgccaag ctgggtatca cagagcctca gactcctgga acaggaactg    960
tgggggtcag gtcagcaggg gaggttaggg agtgttccct ttgtactgac ttagcattta   1020
tcctgcttct aggggggaag gggggccagt gggggatgca cagcaaggca gtgatgtggc   1080
aggcagcctg cgggagctcc tggttcctgg tgtgaaaaag ctgggaagga agagggctgg   1140
gtctggtaag tacagcaggc agttggctcc tgagagtcca agccctgtct agagggtgga   1200
gtgagatttc agagggagag ctaaacgggg tgggggctgg ggagtccagg cttctggctc   1260
ctgctaatac tcagtgtgct gggtcctcag aacctcaggg tggccatttt cagggtgaga   1320
gctctgtcct ttggcacttc tgcagactcc agtatccaga ggaataaaga tggtactctt   1380
cctcagttcc cttagtgaga ggacaccttt ctctgaaggg cttgggcagt tgtcctgaac   1440
cattgcctga aggaaggact tgactccagg gacatagaat gggctcagca taagtcccct   1500
gtagtagaga aggtcccct ctctggtctc cttagagatc ctgtttcctt ggctgaggaa   1560
gctagggtgg atctttgtgt aagtgggtgt ggatgctcac tggaaatcaa aaggccccctt  1620 ggtgttagac cttggggtgc catgggagag ttgatcactg agtgcgccct tacatggggg   1680
ccagctgaga atgggctgc ctctagctcg agaccatgat gcagggagtg agtgggggag    1740
ttcaggatac tcttaactaa agcagaggtc tgtccccca gggaggggag gtcagaagac   1800
cctagggaga tgccaaaggc tagggttggc accatgttgc aggctgtgtc ttcaaggaga   1860
tgataatcag aggaatcgaa cctgcaaaag tgggccagtc ttagatacac tatagaggaa   1920
taatcttctg aaacattctg tgtctcatag gacctgcctg aggacccagc cccagtgcca   1980
gcacatacac tggggcagtg agtagatagt atactttgtt acatgggctg gggggacatg   2040
gcctgtgccc tggaggggac ttgaagacat ccaaaaagct agtgagaggg ctcctagatt   2100
tatttgtctc caagggctat atatagcctt cctaacatga accttgggt aatccagcat    2160 gggcgctccc atatgccctg gtttgattag agagctctag atgtctcctg tcccagaaca   2220
ccagccagcc cctgtcttca tgtcgtgtct agggcggagg gtgattcaga ggcaggtgcc   2280
tgcgacagtg gatgcaatta gatctaatgg gacggaggcc tctctcgtcc gtcgccctcg   2340
ctctgtgccc accccgcct ccctcaggca cagcaggcgt ggagaggatg cgcaggaggt    2400
aggaggtggg ggacccagag gggctttgac gtcagcctgg cctttaagag gccgcctgcc   2460
tggcaagggc tgtggagaca gaactcggga ccaccagctt                         2500
```

<210> SEQ ID NO 2

```
<211> LENGTH: 315
<212> TYPE: DNA
<213> ORGANISM: Mus musculus

<400> SEQUENCE: 2
attagagagc tctagatgtc tcctgtccca gaacaccagc cagcccctgt cttcatgtcg    60
tgtctagggc ggagggtgat tcagaggcag gtgcctgcga cagtggatgc aattagatct   120
aatgggacgg aggcctctct cgtccgtcgc cctcgctctg tgcccacccc cgcctccctc   180
aggcacagca ggcgtggaga ggatgcgcag gaggtaggag gtgggggacc cagagggct    240 ttgacgtcag cctggccttt aagaggccgc ctgcctggca agggctgtgg agacagaact   300
cgggaccacc agctt                                                    315

<210> SEQ ID NO 3
<211> LENGTH: 143
<212> TYPE: DNA
<213> ORGANISM: Mus musculus

<400> SEQUENCE: 3
attagagagc tctagatgtc tcctgtccca gaacaccagc cagcccctgt cttcatgtcg    60
tgtctagggc ggagggtgat tcagaggcag gtgcctgcga cagtggatgc aattagatct   120
aatgggacgg aggcctctct cgt                                           143

<210> SEQ ID NO 4
<211> LENGTH: 67
<212> TYPE: DNA
<213> ORGANISM: Mus musculus

<400> SEQUENCE: 4
ccctgtcttc atgtcgtgtc tagggcggag ggtgattcag aggcaggtgc ctgcgacagt    60
ggatgca                                                              67

<210> SEQ ID NO 5
<211> LENGTH: 100
<212> TYPE: DNA
<213> ORGANISM: Mus musculus

<400> SEQUENCE: 5
aggaggtggg ggacccagag gggctttgac gtcagcctgg cctttaagag gccgcctgcc    60
tggcaagggc tgtggagaca gaactcggga ccaccagctt                         100

<210> SEQ ID NO 6
<211> LENGTH: 93
<212> TYPE: DNA
<213> ORGANISM: Simian virus 40

<400> SEQUENCE: 6
atttatgcag aggccgaggc cgcctcggcc tctgagctat tccagaagta gtgaggaggc    60 tttttttggag gcctaggctt ttgcaaaaag ctt                                93

<210> SEQ ID NO 7
<211> LENGTH: 165
<212> TYPE: DNA
<213> ORGANISM: Simian virus 40

<400> SEQUENCE: 7
ggtgtggaaa gtccccaggc tccccagcag gcagaagtat gcaaagcatg catctcaatt    60
agtcagcaac caggtgtgga aagtccccag gctccccagc aggcagaagt atgcaaagca   120
```
tgcatctcaa ttagtcagca accatagtcc cgcccctaac tccgc 165

<210> SEQ ID NO 8
<211> LENGTH: 758
<212> TYPE: DNA
<213> ORGANISM: Human herpesvirus 1

<400> SEQUENCE: 8

```
gatctaaatg agtcttcgga cctcgcgggg gccgcttaag cggtggttag ggtttgtctg    60
acgcggggggg aggggggaagg aacgaaacac tctcattcgg aggcggctcg ggggtttggtc   120
ttggtggcca cgggcacgca agagagcgcc gcgatcctct taagcacccc cccgccctcc   180
gtggaggcgg gggtttggtc ggcgggtggt aactggcggg ccgctgactc gggcgggtcg   240
cgcgccccag agtgtgacct tttcggtctg ctcgcagacc ccggggcggc gccgccgcgg   300
cggcgacggg ctcgctgggt cctaggctcc atggggaccg tatacgtgga caggctctgg   360
agcatccgca cgactgcggt gatattaccg agaccttct gcgggacgag ccgggtcacg   420
cggctgacgc ggagcgtccg ttgggcgaca aacaccagga cggggcacag gtacactatc   480
ttgtcacccg gaggcgcgag ggactgcagg agcttcaggg agtggcgcag ctgcttcatc   540
cccgtggccc gttgctcgcg tttgctggcg gtgtccccgg aagaaatata tttgcatgtc   600
tttagttcta tgatgacaca aaccccgccc agcgtcttgt cattggcgaa ttcgaacacg   660
cagatgcagt cggggcggcg cggtcccagg tccacttcgc atattaaggt gacgcgtgtg   720
gcctcgaaca ccgagcgacc ctgcagcgac ccgcttaa                            758
```

<210> SEQ ID NO 9
<211> LENGTH: 1836
<212> TYPE: DNA
<213> ORGANISM: Cytomegalovirus

<400> SEQUENCE: 9

```
agatctaaat gagtcttcgg acctcgcggg ggccgcttaa gcggtggtta gggtttgtct    60
gacgcggggg gaggggggaag gaacgaaaca ctctcattcg gaggcggctc ggggtttggt   120
cttggtggcc acgggcacgc agaagagcgc cgcgatcctc ttaagcaccc cccgccctc   180
cgtggaggcg ggggtttggt cggcgggtgg taactggcgg gccgctgact cgggcgggtc   240
gcgcgcccca gagtgtgacc ttttcggtct gctcgcagac cccggggcgg cgccgccgcg   300
gcggcgacgg gctcgctggg tcctaggctc catggggacc gtatacgtgg acaggctctg   360
gagcatccgc acgactgcgg tgatattacc ggagaccttc tgcgggacga gccgggtcac   420
gcggctgacg cggagcgtcc gttgggcgac aaacaccagg acggggcaca ggtacactat   480
cttgtcaccc ggaggcgcga gggactgcag gagcttcagg gagtggcgca gctgcttcat   540
ccccgtggcc cgttgctcgc gtttgctggc ggtgtccccg gaagaaatat atttgcatgt   600
ctttagttct atgatgacac aaaccccgcc cagcgtcttg tcattggcga attcgaacac   660
gcagatgcag tcggggcggc gcggtcccag gtccacttcg catattaagg tgacgcgtgt   720
ggcctcgaac accgagcgac cctgcagcga cccgcttaaa agcttgattc ttctgacaca   780
acagtctcga acttaagctg cagaagttgg tcgtgaggca ctgggcaggt aagtatcaag   840
gttacaagac aggtttaagg agaccaatag aaactgggct tgtcgagaca gagaagactc   900
ttgcgtttct gataggcacc tattggtctt actgacatcc actttgcctt tctctccaca   960
ggtgtccact cccagttcaa ttacagctct taaggctaga gtacttaata cgactcacta  1020
```

```
taggctagcc accatgactt cgaaagttta tgatccagaa caaaggaaac ggatgataac    1080
tggtccgcag tggtgggcca gatgtaaaca atgaatgtt cttgattcat ttattaatta    1140
ttatgattca gaaaaacatg cagaaaatgc tgttattttt ttacatggta acgcggcctc    1200
ttcttattta tggcgacatg ttgtgccaca tattgagcca gtagcgcggt gtattatacc    1260
agaccttatt ggtatgggca atcaggcaa atctggtaat ggttcttata ggttacttga    1320
tcattacaaa tatcttactg catggtttga acttcttaat ttaccaaaga agatcatttt    1380
tgtcggccat gattgggtg cttgtttggc atttcattat agctatgagc atcaagataa    1440
gatcaaagca atagttcacg ctgaaagtgt agtagatgtg attgaatcat gggatgaatg    1500
gcctgatatt gaagaagata ttgcgttgat caaatctgaa gaaggagaaa aatggttttt    1560
ggagaataac ttcttcgtgg aaaccatgtt gccatcaaaa atcatgagaa agttagaacc    1620
agaagaattt gcagcatatc ttgaaccatt caaagagaaa ggtgaagttc gtcgtccaac    1680
attatcatgg cctcgtgaaa tcccgttagt aaaaggtgg aaacctgacg ttgtacaaat    1740
tgttaggaat tataatgctt atctacgtgc aagtgatgat ttaccaaaaa tgtttattga    1800
atcggaccca ggattctttt ccaatgctat tgttga                             1836

<210> SEQ ID NO 10
<211> LENGTH: 2562
<212> TYPE: DNA
<213> ORGANISM: Rattus norvegicus

<400> SEQUENCE: 10
atgagcagcg gcgccaacat cacctatgcc agccgcaagc ggcgcaagcc ggtgcagaaa      60
acagtaaagc ccgtccctgc tgaaggaatt aagtcaaacc cttctaaacg acacagagac     120
cggctgaaca cagagttaga ccgcctggct agcctgctgc ccttcccaca agatgttatt     180
aataagctgg acaaactctc cgttctaagg ctcagcgtca gctacctgag ggccaagagc     240
ttctttgatg ttgcattaaa atccaccccg gctgacagaa gtagaggcca ggaccagtgt     300
agagcacaag tcagagactg gcaggacttg caagaaggag agttcttgtt acaggcgctg     360
aatggctttg ttctggttgt cacggcagat gccttggtct tctatgcgtc ttccactatc     420
caagattacc tgggctttca gcaatctgat gtcatacatc agagcgtgta tgagcttatc     480
catacagaag accgagctga gttccagcgc cagcttcact gggctctaaa cccctcacag     540
tgcacagact ctgcacaagg agtagacgag actcatggcc tcccacagcc agcggtctac     600
tacacgccag accagcttcc tccagagaat accgctttca tggagaggtg cttcagatgc     660
cggctgaggt gcctgctgga taattcatct ggtttcctgg caatgaattt ccaagggagg     720
ttaaagtatc ttcatggaca gaacaagaaa gggaaagacg gagcgctact ccctccacag     780
ttggctttgt ttgcaatagc tactccactt cagccaccgt ccatcctgga aattcgaacc     840
aaaaacttca tcttcaggac caaacacaaa ctggacttca cacctattgg ctgtgatgcc     900
aaagggcagc ttattctggg ctacacagaa gtagagctgt gcaacaaagg atcgggatat     960
cagtttatcc acgccgctga catgcttcac tgcgcagaat cccacatccg catgattaag    1020
actggagaaa gtggcatgac agttttccgg cttcttgcaa aacacagtcg atggaggtgg    1080
gtccagtcca atgcacgctt gatttacaga atggaagac agattacat catcgcaact    1140 cagagaccgc taacggatga agaaggacgc gaacatttac agaagagaag tatgacactg    1200
ccattcatgt ttgccactgg agaggctgta ctgtacgaga tctccagccc ttctctccc    1260 ataatggatc ccttgccaat acgcaccaaa agcaacacta gtaggaaaga ctgggctccc    1320
```

```
cagtcaaccc cgagtaagga ttctttccac cccaattccc ttatgagtgc cttgatccaa    1380
caggacgagt ccatctatct ctgtcctcct tcgagcccg caccattaga cagccatttt    1440
ctcatggact ccatgagtga gtgcggcagt tggcaaggca gctttgcagt cgcaagcaat    1500
gaagctctgc tgaaacacga ggaaatcaga cacactcagg acgtgaacct tacactctct    1560
ggaggcccct cggagctctt cccagataat aaaaataatg acttgtatag catcatgaga    1620
aacctaggga tcgatttcga agacatcaga agcatgcaga atgaggagtt cttccgaacc    1680
gactcctccg gtgaggttga cttcaaagac atcgacataa cagacgaaat cctgacgtac    1740
gtgcaggatt ctctgaacaa ttcaactctg ctgaattcag cttgccagca acagcctgtg    1800
agccagcacc taagctgcat gctgcaggag cgcctgcagc tggagcaaca acagcagctt    1860
cagcagcagc accccactca gacactggag ccccagcgcc agttgtgtca ggtggaggtc    1920
ccccagcacg agctgggtca gaaaacgaag cacatgcaag tcaatggcat gttcgccagt    1980
tggaaccctg cccctcccgt gtctttcagc tgtcctcagc aggaacgaaa gcactatagc    2040
ctcttctccg gcttacaggg gactgcacag gagtttccct acaagtcaga ggtggacagt    2100
atgccttaca cacagaactt tgctccctgc aaccagtcac tgctaccaga acattccaag    2160
ggtacacagt tggacttccc ctggaagggat tttgaacgat ccctgcaccc taacgcttct    2220
aatttagaag actttgtcag ttgtttacaa gttcctgaaa accaaagaca cgggataaac    2280
tcacagtcag ccatggtcag tcctcaggcg tactacgctg ggccatgtc catgtaccag    2340 tgccaggcag ggcctcagca cacccctgtg accagatgc attacagccc tgagattcca    2400
ggctcccagg cgttcctaag caagtttcag agtccgagca ttttaaatga agcctactcg    2460
gcagacttga gcagcattgg ccaccttcag actgctgctc acctcctcg cctggcagaa    2520 gcccagcctc ttcctgatat cacacccagc ggattcctgt ag                      2562

<210> SEQ ID NO 11
<211> LENGTH: 2418
<212> TYPE: DNA
<213> ORGANISM: Mus musculus

<400> SEQUENCE: 11
atgagcagcg cgccaacat cacctatgcc agccgcaagc ggcgcaagcc ggtgcagaaa     60
acagtaaagc ccatccccgc tgaaggaatt aagtcaaatc cttctaagcg acacagagac   120
cggctgaaca cagagttaga ccgcctggcc agcctgctgc ccttcccgca agatgttatt   180
aataagctgg acaaactctc tgttcttagg ctcagcgtca gctacctgag gccaagagc    240 ttctttgatg ttgcattaaa gtccacccct gctgacagaa atggaggcca ggaccagtgt   300
agagcacaaa tcagagactg gcaggattttg caagaaggag agttcttgtt acaggcgctg   360
aatggctttg tgctggttgt cacagcagat gccttggtct tctatgcttc ctccactatc   420
caagattacc tgggctttca gcagtctgat gtcatccatc agagcgtata tgagctcatc   480
catacagaag accgggcgga attccagcgc cagcttcact gggctctaaa cccagactct   540
gcacaaggag tggacgaagc ccatggccct ccacaggcag cagtctatta taccccagac   600
cagcttcctc cagagaacgc ttcttttcatg gagaggtgct tcaggtgccg gctgaggtgc   660
ctgctggata attcatctgg ttttctggca atgaatttcc aagggaggtt aaagtatctt   720
catggacaga acaagaaagg gaaggacgga gcgctgcttc ctccacaact ggctttgttt   780
gcaatagcta ctccacttca gccaccctcc atcctggaaa ttcgaccaa aaacttcatc     840
```

```
ttcaggacca aacacaagct agacttcaca cctattggtt gtgatgccaa agggcagctt      900
attctgggct atacagaagt agagctgtgc acaagaggat cggggtacca gttcatccat      960
gctgcagaca tacttcactg tgcagaatcc cacatccgca tgattaagac tggagaaagt     1020
ggcatgacag ttttccggct tcttgcaaaa cacagtcgct ggaggtgggt ccagtccaat     1080
gcacgcttga tttacagaaa tggaagacca gattacatca tcgccactca gagaccactg     1140
acggatgaag aaggacgaga gcatttacag aagcgaagta cgtcgctgcc cttcatgttt     1200
gctaccggag aggctgtgtt gtacgagatc tccagcccct tctctcccat aatggatccc     1260
ctaccaatac gcaccaaaag caacactagc aggaaagact gggctcccca gtcaacccca     1320
agtaaggatt ctttccaccc cagttctctt atgagtgccc tcatccagca ggatgagtcc     1380
atctatctgt gtcctccttc aagccctgcg ctgttagaca gccatttttct catgggctcc     1440 gtgagcaagt gcgggagttg caagacagc tttgcggccg caggaagtga ggctgcgctg     1500
aaacatgagc aaattggcca tgctcaggac gtgaaccttg cactctctgg cggcccctca     1560
gagctctttc cggataataa aaataatgac ttgtacagca tcatgaggaa ccttgggatt     1620
gattttgaag atatcagaag catgcagaac gaggagttct tcagaactga ctccaccgct     1680
gctggtgagg ttgacttcaa agacatcgac ataacggacg aaatcctgac ctacgtgcag     1740
gattccctga caattcaac tttgctgaac tcggcttgcc agcagcagcc tgtgactcag     1800
cacctaagct gtatgctgca ggagcgcctg caactagagc aacagcaaca gcttcagcag     1860
cccccgccgc aggctctgga gccccagcag cagctgtgtc agatggtgtg cccccagcaa     1920
gatctgggtc cgaagcacac gcaaatcaac ggcacgtttg caagttggaa ccccaccccct     1980 cccgtgtctt tcaactgtcc ccagcaggaa ctaaagcact atcagctctt ttccagctta     2040
caggggactg ctcaggaatt tccctacaaa ccagaggtgg acagtgtgcc ttacacacag     2100
aactttgctc cctgtaatca gcctctgctt ccagaacatt ccaagagtgt gcagttggac     2160
ttccctggaa gggattttga accgtccctg catcccacta cttctaattt agattttgtc     2220
agttgtttac aagttcctga aaaccaaagt catgggataa actcacagtc cgccatggtc     2280
agtcctcagg catactatgc tggggccatg tccatgtatc agtgccagcc agggccacag     2340 cgcaccccctg tggaccagac gcagtacagc tctgaaattc caggttctca ggcattccta     2400
agcaaggtgc agagttga                                                    2418
```

<210> SEQ ID NO 12
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 12
cccaagctta ccatgagcag cggcgccaac atca                                    34

<210> SEQ ID NO 13
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 13
ccgctcgaga ggaatccgct gggtgtgata tcag                                    34

<210> SEQ ID NO 14
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 14
cccaagctta tgagcagcgg cgccaacatc acc                         33

<210> SEQ ID NO 15
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 15
ccctctagat caactctgca ccttgcttag gaa                         33

<210> SEQ ID NO 16
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 16
cgcggtaccc ttctctgtgc ccacagatgc ttta                        34

<210> SEQ ID NO 17
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 17
gcagctagca agctggtggt cccgagttct gtct                        34

<210> SEQ ID NO 18
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 18
cgcggtacct gggtttgcct caccctgcaa tccc                        34

<210> SEQ ID NO 19
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 19
ccaggtaccg aggttaggga gtgttccctt tgta                        34

<210> SEQ ID NO 20
<211> LENGTH: 34
<212> TYPE: DNA
<213> ORGANISM: Artificial Sequence
<220> FEATURE:
<223> OTHER INFORMATION: Synthetic Oligonucleotide
<210> SEQ ID NO 20
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 20
cagggtaccg ctcagcataa gtccctgta gtag                                   34

<210> SEQ ID NO 21
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 21
cgtggtacca catacactgg ggcagtgagt agat                                   34

<210> SEQ ID NO 22
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 22
cggggtacca gatttatttg tctccaaggg ctat                                   34

<210> SEQ ID NO 23
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 23
cggggtacca ttagagagct ctagatgtct cctg                                   34

<210> SEQ ID NO 24
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 24
cccggtaccc taatgggacg gaggcctctc tcgt                                   34

<210> SEQ ID NO 25
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 25
cggggtaccg tgggggaccc agagggctt tgac                                    34

<210> SEQ ID NO 26
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 26
gccgctagca cgagagaggc ctccgtccca ttag                                   34

<210> SEQ ID NO 27
<211> LENGTH: 34

```
<212> TYPE: DNA
<213> ORGANISM: Artificial Sequence
<220> FEATURE:
<223> OTHER INFORMATION: Synthetic Oligonucleotide

<400> SEQUENCE: 27
cggctcgagg tgggggaccc agagggggctt tgac                            34

<210> SEQ ID NO 28
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 28
gcaaagctta agctggtggt cccgagttct gtct                             34

<210> SEQ ID NO 29
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 29
agcggtaccc tgtcttcatg tcgtgtctag g                                31

<210> SEQ ID NO 30
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 30
agcgctagct gcatccactg tcgcaggcac c                                31

<210> SEQ ID NO 31
<211> LENGTH: 13
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (6)..(8)
<223> OTHER INFORMATION: a, t, c, g, unknown or other

<400> SEQUENCE: 31
ggtcannntg acc                                                    13

<210> SEQ ID NO 32
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (7)..(9)
<223> OTHER INFORMATION: a, t, c, g, unknown or other

<400> SEQUENCE: 32
ggwacannnt gttct                                                  15
```